United States Patent
DeVries et al.

(10) Patent No.: US 10,877,008 B2
(45) Date of Patent: Dec. 29, 2020

(54) REFERENCE GAS MANAGEMENT IN A BREATH ALCOHOL CALIBRATION STATION

(71) Applicant: Consumer Safety Technology, LLC, Des Moines, IA (US)

(72) Inventors: Douglas Edward DeVries, Johnston, IA (US); Scott Ruland, Kansas City, MO (US)

(73) Assignee: Consumer Safety Technology, LLC, Des Moines, IA (US)

( * ) Notice: Subject to any disclaimer, the term of this patent is extended or adjusted under 35 U.S.C. 154(b) by 90 days.

(21) Appl. No.: 15/261,231

(22) Filed: Sep. 9, 2016

(65) Prior Publication Data

US 2018/0074029 A1   Mar. 15, 2018

(51) Int. Cl.
*G01N 33/00* (2006.01)
*G01N 33/497* (2006.01)

(52) U.S. Cl.
CPC ..... *G01N 33/0006* (2013.01); *G01N 33/4972* (2013.01)

(58) Field of Classification Search
CPC .............. G01N 33/0006; G01N 33/4972
USPC ..................................... 73/1.03
See application file for complete search history.

(56) References Cited

U.S. PATENT DOCUMENTS

| | | |
|---|---|---|
| 3,824,167 A | 7/1974 | Oswin et al. |
| 3,847,551 A | 11/1974 | Hutson et al. |
| 3,854,319 A | 12/1974 | Burroughs et al. |
| 3,877,291 A | 4/1975 | Hoppesch et al. |

(Continued)

FOREIGN PATENT DOCUMENTS

| | | |
|---|---|---|
| AU | 2001097152 | 6/2002 |
| AU | 2011256122 | 12/2013 |

(Continued)

OTHER PUBLICATIONS

"Calibration Station for the Ventis™ MX4: Product Manual," Industrial Scientific Corporation, 2010 (40 pages).
"MicroDock II Automatic Test and Calibration Station User Manual," BW Technologies by Honeywell, 2009 (101 pages).
"SDM-2012 Docking Station Standalone Configuration Operators Manual," RKI Instruments, released Aug. 12, 2013 (112 pages).

(Continued)

*Primary Examiner* — Nimeshkumar D Patel
*Assistant Examiner* — Nashmiya S Fayyaz
(74) *Attorney, Agent, or Firm* — Pauly, DeVries Smith & Deffner LLC

(57) ABSTRACT

A breath alcohol device calibration system includes a computerized calibration module operable to calibrate a candidate breath alcohol device using a reference gas of known alcohol concentration, and a reference gas tank identification module operable to identify a reference gas tank that is coupled to the breath alcohol device calibration system. Identification is performed using at least one distinguishing characteristic of the coupled tank, the distinguishing characteristic providing reference gas tank information including at least the known alcohol concentration of gas in the reference gas tank. The reference gas tank identification module is further operable to read a temperature history of the tank from an electronic device coupled to the tank, and to indicate an error condition if the temperature history of the tank indicates temperatures below a first temperature threshold over the tank's recent temperature history to potentially result in incomplete mixing of the reference gas.

20 Claims, 7 Drawing Sheets

(56) References Cited

U.S. PATENT DOCUMENTS

| | | |
|---|---|---|
| 3,948,604 A | 4/1976 | Hoppesch et al. |
| 4,034,743 A | 7/1977 | Greenwood et al. |
| 4,278,636 A | 7/1981 | Boldt et al. |
| 4,407,152 A | 10/1983 | Guth et al. |
| 4,448,058 A | 5/1984 | Jaffe et al. |
| 4,481,804 A | 11/1984 | Eberhard et al. |
| 4,487,055 A | 12/1984 | Wolf et al. |
| 4,592,443 A | 6/1986 | Simon |
| 4,656,008 A | 4/1987 | Gump |
| 4,678,057 A | 7/1987 | Elfman et al. |
| 4,680,956 A | 7/1987 | Huszczuk |
| 4,697,666 A | 10/1987 | Collier et al. |
| 4,722,217 A | 2/1988 | Arnett et al. |
| 4,749,553 A | 6/1988 | Phillips et al. |
| 4,809,810 A | 3/1989 | Elfman et al. |
| 4,854,153 A | 8/1989 | Miyagawa et al. |
| 4,901,058 A | 2/1990 | Comeau et al. |
| 4,912,458 A | 3/1990 | Comeau et al. |
| 4,914,038 A | 4/1990 | Jewitt et al. |
| 4,970,172 A | 11/1990 | Kundu |
| 5,058,601 A | 10/1991 | Riker |
| 5,069,220 A | 12/1991 | Casparie et al. |
| 5,134,875 A | 8/1992 | Jensen et al. |
| 5,239,492 A * | 8/1993 | Hartwig ............ G01N 33/0006 702/27 |
| 5,303,575 A | 4/1994 | Brown et al. |
| 5,303,712 A | 4/1994 | Van |
| 5,400,637 A | 3/1995 | Forrester et al. |
| 5,422,485 A | 6/1995 | Bowlds |
| 5,426,415 A | 6/1995 | Prachar et al. |
| 5,443,794 A | 8/1995 | Williams |
| 5,493,891 A | 2/1996 | Slemeyer |
| 5,622,164 A | 4/1997 | Kilis et al. |
| 5,665,894 A | 9/1997 | Baker |
| 5,705,735 A | 1/1998 | Acorn |
| 5,734,090 A | 3/1998 | Koppel et al. |
| 5,866,794 A | 2/1999 | Stock |
| 6,026,674 A | 2/2000 | Gammenthaler et al. |
| 6,075,444 A | 6/2000 | Sohege et al. |
| 6,079,251 A | 6/2000 | Gaultier et al. |
| 6,096,558 A | 8/2000 | Stock et al. |
| 6,167,746 B1 | 1/2001 | Gammenthaler |
| 6,174,289 B1 | 1/2001 | Binder |
| 6,206,130 B1 | 3/2001 | Hetler et al. |
| 6,206,837 B1 | 3/2001 | Brugnoli |
| 6,244,093 B1 | 6/2001 | Parekh |
| 6,442,639 B1 | 8/2002 | McElhattan et al. |
| 6,475,158 B1 | 11/2002 | Orr et al. |
| 6,526,802 B1 | 3/2003 | Guth et al. |
| 6,611,201 B1 | 8/2003 | Bishop et al. |
| 6,656,127 B1 | 12/2003 | Ben-oren et al. |
| 6,664,888 B1 | 12/2003 | Bishop et al. |
| 6,748,792 B1 | 6/2004 | Freund et al. |
| 6,824,520 B2 | 11/2004 | Orr et al. |
| 6,853,956 B2 | 2/2005 | Ballard et al. |
| 6,918,281 B2 | 7/2005 | Sussman et al. |
| 6,956,484 B2 | 10/2005 | Crespo et al. |
| 6,980,124 B2 | 12/2005 | Kong et al. |
| 7,061,137 B2 | 6/2006 | Flick et al. |
| 7,103,454 B2 | 9/2006 | Stock et al. |
| 7,132,659 B2 | 11/2006 | Starta et al. |
| 7,132,762 B2 | 11/2006 | Metlitzky et al. |
| 7,135,788 B2 | 11/2006 | Metlitzky et al. |
| 7,204,335 B2 | 4/2007 | Stewart et al. |
| 7,218,236 B2 | 5/2007 | Mcmillin et al. |
| 7,222,006 B2 | 5/2007 | Proefke et al. |
| 7,256,700 B1 | 8/2007 | Ruocco et al. |
| 7,260,976 B2 | 8/2007 | Colman et al. |
| 7,287,617 B2 | 10/2007 | Mobley et al. |
| 7,299,890 B2 | 11/2007 | Mobley et al. |
| 7,329,390 B2 | 2/2008 | Chrzan et al. |
| 7,341,693 B2 | 3/2008 | Der et al. |
| 7,351,954 B2 | 4/2008 | Zhang et al. |
| 7,359,773 B2 | 4/2008 | Simon et al. |
| 7,377,147 B1 | 5/2008 | Scheffler et al. |
| 7,377,352 B2 | 5/2008 | Mobley et al. |
| 7,400,258 B2 | 7/2008 | Crespo et al. |
| 7,401,493 B2 | 7/2008 | Forrest |
| 7,404,311 B2 | 7/2008 | Guth et al. |
| 7,422,723 B1 | 9/2008 | Betsill et al. |
| 7,451,852 B2 | 11/2008 | Stewart et al. |
| 7,481,292 B2 | 1/2009 | Mobley et al. |
| 7,483,805 B2 | 1/2009 | Sparks et al. |
| 7,493,792 B2 | 2/2009 | Bouchoux et al. |
| 7,493,793 B2 | 2/2009 | Guth et al. |
| 7,519,326 B2 | 4/2009 | Thomas et al. |
| 7,530,851 B2 | 5/2009 | Parnis et al. |
| 7,541,192 B2 | 6/2009 | Stock |
| 7,543,472 B2 | 6/2009 | Crespo et al. |
| 7,603,887 B2 | 10/2009 | Schlichte et al. |
| 7,658,255 B2 | 2/2010 | Nordin |
| 7,743,647 B1 | 6/2010 | Israel et al. |
| 7,797,982 B2 | 9/2010 | Burke et al. |
| 7,823,681 B2 | 11/2010 | Crespo et al. |
| 7,841,224 B2 | 11/2010 | Son |
| 7,860,677 B2 | 12/2010 | Artiuch |
| 7,895,878 B1 | 3/2011 | Guth et al. |
| 7,934,577 B2 | 5/2011 | Devries et al. |
| 8,001,825 B2 | 8/2011 | Pugh et al. |
| 8,059,003 B2 | 11/2011 | Roth |
| 8,197,417 B2 | 6/2012 | Howard et al. |
| 8,224,608 B1 | 7/2012 | Son et al. |
| 8,240,419 B2 | 8/2012 | Zimmermann et al. |
| 8,250,900 B2 | 8/2012 | Son |
| 8,311,858 B2 | 11/2012 | Mcmillan et al. |
| 8,317,998 B2 | 11/2012 | Pratt et al. |
| 8,326,484 B2 | 12/2012 | Mcgarry et al. |
| 8,359,901 B2 | 1/2013 | Freund et al. |
| 8,364,431 B2 | 1/2013 | Russell et al. |
| 8,418,523 B2 | 4/2013 | Lueck et al. |
| 8,505,360 B2 | 8/2013 | Ruocco et al. |
| 8,515,704 B2 | 8/2013 | Son et al. |
| 8,667,829 B2 | 3/2014 | Guth et al. |
| 8,688,073 B2 | 4/2014 | Peisa et al. |
| 8,701,815 B2 | 4/2014 | Polzius et al. |
| 8,713,985 B2 | 5/2014 | Lueck et al. |
| D708,757 S | 7/2014 | Shibata |
| 8,795,187 B2 | 8/2014 | Morley et al. |
| 8,800,708 B2 | 8/2014 | Morley et al. |
| 8,822,929 B2 | 9/2014 | Nesa et al. |
| 8,918,251 B2 | 12/2014 | Tarnutzer et al. |
| 8,957,771 B2 | 2/2015 | Devries et al. |
| 9,020,773 B2 | 4/2015 | Son et al. |
| 9,103,818 B2 | 8/2015 | Son |
| 9,128,067 B2 | 9/2015 | Ostermann et al. |
| 9,140,685 B2 | 9/2015 | Christman et al. |
| 9,207,223 B2 | 12/2015 | Arias et al. |
| 9,221,339 B2 | 12/2015 | Comeau |
| 9,260,012 B2 | 2/2016 | Lopez et al. |
| 9,261,885 B2 | 2/2016 | Tryfonos et al. |
| 9,308,892 B2 | 4/2016 | Schwarz et al. |
| 9,311,758 B2 | 4/2016 | Choi |
| 9,371,056 B2 | 6/2016 | Lunstedt et al. |
| 9,376,017 B2 | 6/2016 | Bailey et al. |
| 9,417,232 B2 | 8/2016 | Keays et al. |
| 9,475,459 B2 | 10/2016 | Tieman |
| 9,481,245 B2 | 11/2016 | Nelson et al. |
| 9,488,672 B2 | 11/2016 | Macdonald |
| 9,518,966 B2 | 12/2016 | Duric et al. |
| 9,562,883 B2 | 2/2017 | Silverman et al. |
| 9,562,889 B2 | 2/2017 | Son et al. |
| 9,562,890 B2 | 2/2017 | Son |
| 9,662,976 B2 | 5/2017 | Comeau et al. |
| 9,746,456 B2 | 8/2017 | Keays et al. |
| 9,772,318 B1 | 9/2017 | Lyon |
| 9,784,755 B2 | 10/2017 | Scheffler et al. |
| 10,132,786 B2 | 11/2018 | Diekmann |
| 10,222,367 B2 | 3/2019 | Tschuncky et al. |
| 10,458,975 B1 | 10/2019 | Lyon |
| 10,663,440 B2 | 5/2020 | Devries |
| 2001/0037070 A1 | 11/2001 | Cranley et al. |
| 2002/0127145 A1 | 9/2002 | Der Ghazarian et al. |
| 2003/0000281 A1 | 1/2003 | Ketler et al. |
| 2003/0167821 A1 | 9/2003 | Sussman et al. |

(56) References Cited

U.S. PATENT DOCUMENTS

| | | |
|---|---|---|
| 2003/0216660 A1 | 11/2003 | Ben-oren et al. |
| 2004/0055359 A1 | 3/2004 | Ketler et al. |
| 2004/0074279 A1 | 4/2004 | Forrest |
| 2005/0000981 A1 | 1/2005 | Peng et al. |
| 2005/0273016 A1 | 12/2005 | Colman et al. |
| 2006/0081033 A1 | 4/2006 | Peng |
| 2006/0156789 A1 | 7/2006 | Frank et al. |
| 2006/0263254 A1 | 11/2006 | Lee |
| 2007/0044534 A1 | 3/2007 | Forrest et al. |
| 2007/0062249 A1 | 3/2007 | Forrest |
| 2007/0144812 A1 | 6/2007 | Stewart et al. |
| 2007/0261468 A1 | 11/2007 | Crespo et al. |
| 2008/0154535 A1 | 6/2008 | Sparks et al. |
| 2009/0004054 A1 | 1/2009 | Burke et al. |
| 2009/0056408 A1 | 3/2009 | Tryfonos et al. |
| 2009/0153296 A1 | 6/2009 | Legasse et al. |
| 2009/0205407 A1 | 8/2009 | Marhefka et al. |
| 2009/0227887 A1 | 9/2009 | Howard et al. |
| 2010/0012417 A1 | 1/2010 | Walter et al. |
| 2010/0042333 A1 | 2/2010 | Scheffler et al. |
| 2010/0223975 A1 | 9/2010 | Lueck et al. |
| 2011/0084820 A1 | 4/2011 | Walter et al. |
| 2011/0178420 A1 | 7/2011 | Ridder et al. |
| 2011/0283770 A1 | 11/2011 | Hok et al. |
| 2011/0292209 A1 | 12/2011 | Morley et al. |
| 2011/0309932 A1 | 12/2011 | Arringdale et al. |
| 2012/0125076 A1 | 5/2012 | Tryfonos et al. |
| 2012/0209634 A1 | 8/2012 | Ling et al. |
| 2012/0291517 A1 | 11/2012 | Son et al. |
| 2013/0074575 A1* | 3/2013 | Duric ............... G01N 33/0006 73/1.03 |
| 2013/0203365 A1 | 8/2013 | Tieman et al. |
| 2013/0281873 A1 | 10/2013 | Evans et al. |
| 2013/0325924 A1 | 12/2013 | Moshfeghi |
| 2014/0041436 A1 | 2/2014 | Knott et al. |
| 2014/0061043 A1 | 3/2014 | Stock et al. |
| 2014/0076022 A1 | 3/2014 | Ohlsson et al. |
| 2014/0230518 A1 | 8/2014 | Lueck et al. |
| 2014/0260509 A1* | 9/2014 | Pohl ............... G01N 30/02 73/1.02 |
| 2014/0311214 A1 | 10/2014 | Wolf et al. |
| 2014/0311215 A1 | 10/2014 | Keays et al. |
| 2014/0358020 A1* | 12/2014 | Park ............... G01N 33/98 600/532 |
| 2015/0008063 A1 | 1/2015 | Walter et al. |
| 2015/0021113 A1 | 1/2015 | Lefebvre et al. |
| 2015/0070340 A1 | 3/2015 | Trachtenberg et al. |
| 2015/0079685 A1* | 3/2015 | Pfeiffer ............... B01F 11/0022 436/68 |
| 2015/0081134 A1 | 3/2015 | Burger |
| 2015/0160190 A1 | 6/2015 | Ravishankar |
| 2015/0164416 A1 | 6/2015 | Nothacker et al. |
| 2015/0183386 A1 | 7/2015 | Tieman |
| 2015/0187147 A1 | 7/2015 | Tieman |
| 2015/0197151 A1 | 7/2015 | Ballard |
| 2015/0222349 A1 | 8/2015 | Sloan et al. |
| 2015/0244452 A1 | 8/2015 | Wojciech et al. |
| 2015/0251660 A1 | 9/2015 | Nelson |
| 2015/0297117 A1 | 10/2015 | Park et al. |
| 2016/0003746 A1 | 1/2016 | Mccrary et al. |
| 2016/0054296 A1 | 2/2016 | Son |
| 2016/0065298 A1 | 3/2016 | Nakagawa et al. |
| 2016/0086021 A1 | 3/2016 | Grohman et al. |
| 2016/0089976 A1 | 3/2016 | Comeau |
| 2016/0188964 A1 | 6/2016 | Quddus et al. |
| 2016/0229413 A1 | 8/2016 | Morley et al. |
| 2016/0252492 A1 | 9/2016 | Rarama et al. |
| 2016/0327541 A1 | 11/2016 | Reinstaedtler |
| 2016/0377597 A1 | 12/2016 | Tschuncky et al. |
| 2018/0011068 A1 | 1/2018 | Lyon |
| 2019/0072531 A1 | 3/2019 | DeVries et al. |
| 2019/0076056 A1 | 3/2019 | Carlson et al. |
| 2019/0145956 A1 | 5/2019 | Lyon |

FOREIGN PATENT DOCUMENTS

| | | |
|---|---|---|
| CA | 1337463 | 10/1995 |
| CA | 2269546 | 4/1998 |
| CA | 2270809 | 10/1999 |
| CA | 2731040 | 1/2010 |
| CA | 2711410 | 1/2012 |
| CA | 2788785 | 2/2013 |
| CA | 2780135 | 12/2013 |
| CA | 2821197 | 1/2015 |
| CA | 2858708 | 2/2015 |
| CA | 2905093 | 9/2015 |
| CA | 2684266 | 3/2017 |
| CN | 102397616 | 4/2012 |
| CN | 102778541 | 11/2012 |
| CN | 102955472 | 3/2013 |
| CN | 101821120 | 11/2013 |
| CN | 103578853 | 2/2014 |
| DE | 102013015826 | 3/2015 |
| DE | 102013018663 | 5/2015 |
| DE | 202015009104 | 11/2016 |
| EP | 1591296 | 11/2005 |
| EP | 1892648 | 2/2008 |
| EP | 1933218 | 6/2008 |
| EP | 1987355 | 2/2012 |
| EP | 2127599 | 3/2012 |
| EP | 2544000 | 1/2013 |
| EP | 2623378 | 8/2013 |
| EP | 2808681 | 12/2014 |
| EP | 2867666 | 10/2016 |
| EP | 2761267 | 11/2016 |
| EP | 3116736 | 7/2019 |
| ES | 2660013 | 3/2018 |
| GB | 2049193 | 12/1980 |
| GB | 2313198 | 11/1997 |
| IN | 201102479 | 12/2011 |
| KR | 20100070199 | 6/2010 |
| KR | 20100072578 | 7/2010 |
| KR | 101059978 | 8/2011 |
| TW | 565696 A * | 12/2003 |
| WO | 8702773 | 5/1987 |
| WO | 9212416 | 7/1992 |
| WO | 9422686 | 10/1994 |
| WO | 1994022686 | 10/1994 |
| WO | 9641428 | 12/1996 |
| WO | 9714947 | 4/1997 |
| WO | 1998027416 | 6/1998 |
| WO | 2001075439 | 10/2001 |
| WO | 2001086286 | 11/2001 |
| WO | 2002048705 | 6/2002 |
| WO | 2002085706 | 10/2002 |
| WO | 2007059263 | 5/2007 |
| WO | 2007094712 | 8/2007 |
| WO | 2009111484 | 9/2009 |
| WO | 2010009406 | 4/2010 |
| WO | 2010086557 | 8/2010 |
| WO | 2010093317 | 8/2010 |
| WO | 2010094967 | 8/2010 |
| WO | 2010025478 | 3/2011 |
| WO | 2011143693 | 11/2011 |
| WO | 2013001265 | 1/2013 |
| WO | 2013051992 | 4/2013 |
| WO | 2013134460 | 9/2013 |
| WO | 2013191634 | 12/2013 |
| WO | 2014036088 | 3/2014 |
| WO | 2014134252 | 9/2014 |
| WO | 2015100166 | 7/2015 |
| WO | 2015116821 | 8/2015 |
| WO | 2016187243 | 11/2016 |

OTHER PUBLICATIONS

"Non-Final Office Action," for U.S. Appl. No. 15/261,253 dated Aug. 9, 2018 (27 pages).

"Response to Non Final Office Action," for U.S. Appl. No. 15/261,253, filed Nov. 2, 2018 (10 pages).

"Final Office Action," for U.S. Appl. No. 15/261,253 dated Mar. 7, 2019 (17 pages).

(56) References Cited

OTHER PUBLICATIONS

"Accuracy Check Methods Webpage," Intoximeters, Inc., 2013, available as early as Jan. 29, 2013 (1 page).
"ACS Alcosim Calibration Bench Multi Stage Breath Alcohol Simulator," https://acs-corp.com/image/brochures/20171208-BRO-ACS-CA-ENG-A5-ALCOSIMCalibrationBench-WEB.pdf Dec. 8, 2017, 2 pages.
"ACS Metrological Test Bench Multi Stage Breath Alcohol Simulator," https://acs-corp.com/image/brochures/20180129-BRO-ACS-CA-ENG-A5-MetrologicalTestBench-WEB.pdf Jan. 29, 2018, 2 pages.
"Alcolizer LE Main Web Page," Alcolizer Pty Ltd, www.alcolizer.com, available as early as Mar. 20, 2012 (2 pages).
"Alcolizer Re-Calibration Web Page," Alcolizer Pty Ltd, www.alcolizer.com/products/re-calibration, available as early as Mar. 20, 2012 (2 pages).
"Alcolizer Technology Industry Welcome to the AOD Industry Presentation," http://transafewa.com.au/wp-content/uploads/2014/11/Alcolizer-Technology-Industry-Presentation-JY-1509.pdf available at least as early as Mar. 20, 2015, 20 pages.
"Alcolizer Wall Mount Product Page," Alcolizer Pty Ltd, www.alcolizer.com/products/alcolizer-wm-wall-mount-series, available as early as Mar. 20, 2012 (2 pages).
"Alco-Sensor FST Operators Manual," Intoximeters, Inc., printed Jun. 2007 (37 pages).
"Alco-Sensor FST(R) Product Webpage," Intoximeters, Inc., available as early as Dec. 2, 2011 (2 pages).
"Alert J4X.ec Breath Alcohol Tester User Guide," Alcohol Countermeasure Systems, 2008 (36 pages).
"AutoRAE 2 Automatic Test and Calibration System Datasheet," RAE Systems, Inc., DS-1083-02, date unavailable (2 pages).
"AutoRAE 2 Automatic Test and Calibration System User's Guide," RAE Systems by Honeywell, Rev. E, Apr. 2014 (118 pages).
"AutoRAE Lite for QRAE II User's Guide," Rae Systems by Honeywell, Rev. A. Jun. 2009 (55 pages).
"Benefits of Alcosystems iBAC Solution," iBac Alcosystems AB, available online as early as Jan. 11, 2012 (2 pages).
"Bid Specifications: Galaxy(TM) Automated Test System," Mine Safety Appliances Company, available as early as Jul. 11, 2012 (4 pages).
"Breath Alcohol Testing Calibration Equipment Webpage," Intoximeters, Inc., www.intox.com/c-18-calibration.aspx, available as early as Feb. 13, 2012 (2 pages).
"Calibration Device and Method for Calibrating an Ignition Interlock Device," U.S. Appl. No. 14/706,402, filed May 7, 2015 (36 pages).
"Calibration Station or Docking Station: Which one do you need for your gas detectors?," Industrial Scientific Corporation, 2015 (8 pages).
"Description of Calibration Kiosk used for Intoxalock Breath Alcohol Detectors," Intoxalock Description as early as Jan. 2011, 4 pages.
"Draeger Gas Detection Product Brochure," Draeger Safety, Inc, 2009 (50 pages).
"Draeger INTERLOCK(R) XT Product Webpage," Draeger Safety, Inc, www.draeger.us/sites/enus_us/Pages/Law-Enforcement/INTERLOCK-XT.aspx?navID=173, available as early as Apr. 26, 2012 (2 pages).
"Draeger Introduces X-Dock, a Test and Calibration Station for Portable Gas Detection," Press Release, Draeger Safety, Inc., Apr. 23, 2013 (2 pages).
"Draeger Product Selector Webpage," Draeger Safety, Inc, http://www.draeger.us/sites/enus_us/Pages/LawEnforcement/ProductSelector.aspx?navID=159, available as early as Apr. 26, 2012 (2 pages).
"Draeger X-am 2500 Technical Manual," Draeger Safety, Inc, Nov. 2012 (36 pages).
"Draeger X-dock 5300, 6300/6600 Technical Manual," Draeger Safety, Inc., Aug. 2013 (28 pages).
"Draeger X-Dock 5300/6300/6600 Product Brochure," Draeger Safety, Inc, 2012 (5 pages).

"Dry Gas Standard Webpage," Intoximeters, Inc., www.intox.com/t-DryGasStandard.aspx, available as early as Jan. 29, 2013 (2 pages).
"DS2: Administrator's Guide to the DS2 Docking Station," Industrial Scientific Corporation, Nov. 11, 2008 (261 pages).
"Galaxy (R) GX2 Automated Test System Quick Start Guide—Description and Setup," Mine Safety Appliances Company, Sep. 2012 (10 pages).
"Galaxy GX2 Automated Test System Frequently Asked Questions," Mine Safety Appliances Company, Published Aug. 2012 (1 page).
"Galaxy(R) Automated Test System Operating Manual," Mine Safety Appliances Company 2008, available online as early as Jul. 11, 2012 (124 pages).
"Galaxy(R) Automated Test System Product Brochure," Mine Safety Appliances Company, Sep. 2011 (4 pages).
"Galaxy(R) GX2—Simplicity Counts," Product Brochure, Mine Safety Appliances, Aug. 2012 (2 pages).
"Galaxy(R) GX2 Automated Test System Datasheet," Mine Safety Appliances Company, published Aug. 2012 (6 pages).
"Galaxy(R) GX2 Automated Test System Operating Manual," Mine Safety Appliances Company 2012 (72 pages).
"Galaxy(R) Network Interface and Network Manager Instruction Manual," Mine Safety Appliances Company 2010, available online as early as Jul. 11, 2012 (69 pages).
"Guardian Interlock Product WR3 Calibration Station," https://www.guardianinterlock.com.au/product/wr3-calibration-station Available at least as early as Mar. 11, 2015, 3 pages.
"Highway Safety Programs; Conforming Products List of Calibrating Units for Breath Alcohol Testers," Department of Transportation National Highway Traffic Safety Administration. Federal Register / vol. 77, No. 204 / Monday, Oct. 22, 2012 (3 pages).
Hök, Bertil et al., "Breath Analyzer for Alcolocks and Screening Devices," IEEE Sensors Journal, vol. 10, No. 1, Jan. 10-15, 2010 (6 pages).
"Honeywell Biosystems Toxi IQ Express Docking Station ToxiPro Single Gas Detectors," https://www.brandtinst.com/biosystems/detector/IQExpress/index.html available at least as early as Jan. 20, 2008, 3 pages.
"Honeywell IQ Management System," https://www.honeywellanalytics.com/en/products/IQ-Management-System available at least as early as Oct. 18, 2014, 3 pages.
"iBAC Product Brochure," iBac Alcosystems AB, 2011 (6 pages).
"Interlock Help Webpage," Alcohol Countermeasure Systems (International), Inc., www.interlockhelp.com, available as early as Dec. 27, 2011 (1 page).
"Intox DMT Product Brochure," Intoximeters, Inc., printed May 2019 (2 pages).
"Intox EC/IR II Training Materials, Feb. 22-25, 2010," Intoximeters Inc. Jun. 29, 2009, pp. 1-240.
"Intox EC/IR(R) II Webpage," Intoximeters, Inc., www.intox.com/p-562-intox-ecir-ii.aspx, available as early as Sep. 21, 2011 (1 page).
"Intoxilyzer 8000 Reference Guide," Florida Department of Law Enforcement Alcohol Testing Program, Feb. 2006 (14 pages).
"Intoxilyzer 9000 Brochure," CMI, Inc., available at least as early as Feb. 1, 2015 as shown on the Way Back Machine available online., 2 pages.
Jonsson, A. et al., "Development of a Breath Alcohol Analyzer for Use on Patients in Emergency Care," Dössel O., Schlegel W.C. (eds) World Congress on Medical Physics and Biomedical Engineering, Sep. 7-12, 2009 (4 pages).
"LifeSafer Ignition Interlock Webpage," LifeSafer, www.lifesafer.com/, available as early as Jul. 19, 2012 (3 pages).
"Lion Alcometer(R) 500 User Handbook," Lion Laboratories Limited, 2011 (54 pages).
"Method for Calibrating an Ignition Interlock Device," U.S. Appl. No. 14/036,343, filed Sep. 25, 2013 (31 pages).
"Operating the DataMaster DMT," Version 1.0, Division of Criminal Investigation, Alcohol Section, Jul. 2009 (163 pages).
"Response to Final Office Action," for U.S. Appl. No. 15/261,253, filed Sep. 9, 2019 (14 pages).

(56) References Cited

OTHER PUBLICATIONS

"RKI Instruments Docking and Callibration Station Gas Detection for Live SDM-E2," https://www.rkiinstruments.com/pdf/sdme2.pdf available at least as early as Mar. 29, 2014, 2 pages.
Semedo, Daniela "Rapid Breath Test Patented for Potential Quick Diagnosis of TB and Other Lung Diseases," Lung Disease News https://lungdiseasenews.com/2016/01/13/rapid-diagnostic-test-takes-on-tuberculosis-and-other-deadly-diseases/ Jan. 13, 2016, 8 pages.
"Solaris(R) MultiGas Detector Operating Manual," Mine Safety Appliances Company 2007 (162 pages).
"Tim(R) Total Instrument Manager Instruction Manual," Mine Safety Appliances Company 2002 (87 pages).
"True-Cal II Product Webpage," Intoximeters, Inc., http://www.intox.com/p-723-true-cal-ii.aspx, available as early as Sep. 15, 2013 (1 page).
"TruTouch Technologies FAQ Webpage," TruTouch Technologies Inc., www.tttinc.com/FAQ.php, available as early as Dec. 22, 2012 (4 pages).
"TruTouch Technologies Webpage," TruTouch Technologies Inc., www.tttinc.com, available as early as May 19, 2012 (1 page).
Van Tassel, William E. "An Evaluation of Pocket-Model, Numerical Readout Breath Alcohol Testing Instruments," Dissertation Submitted to Texas A&M University, Aug. 2003 (164 pages).
"Where Did the Ignition Interlock Device Come From? A History," https://www.smartstartinc.com/blog/history-ignition-interlock-device/ Aug. 15, 2017, 8 pages.
Wood, Chris "Breathometer Turns Your Smartphone Into a Breathalyzer," New Atlas, https://newatlas.com/breathometer-smartphone-breathalyzer/26634/, Mar. 13, 2013 (4 pages).
"Non-Final Office Action," for U.S. Appl. No. 15/261,253 dated Dec. 12, 2019 (35 pages).
"Non-Final Office Action," for U.S. Appl. No. 16/183,475 dated Mar. 2, 2020 (47 pages).
"Response to Non Final Office Action," for U.S. Appl. No. 15/261,253, filed Feb. 25, 2020 (11 pages).
"Alcohol Monitoring-Scram LinkedIn SlideShare and Presentation," NCSCCLE & NCAJ DUI DWI MASTERS—Continuing Legal Education Sep. 21, 2015, 104 pages.
"ECBA Lunch-n-Learn Smart Start Nuts & Bolts Event Details and Presentation," Erie County Bar Association Feb. 26, 2019, 51 pages.
"Final Office Action," for U.S. Appl. No. 16/183,475 dated Apr. 28, 2020 (21 pages).
"Response to Non Final Office Action," for U.S. Appl. No. 16/183,475, filed Apr. 17, 2020 (9 pages).
"Response to Non Final Office Action," for U.S. Appl. No. 16/183,475, filed Jul. 15, 2020 (12 pages).
"Highway Safety Programs; Model Specifications for Calibrating Units for Breath Alcohol Testers; Conforming Products List of Calibrating Units for Breath Alcohol Testers," Federal Register, vol. 72, No. 121 (Jun. 25, 2007) (7 pages).
"Highway Safety Programs; Model Specifications for Calibrating Units for Breath Alcohol Testers; Conforming Products List of Calibrating Units," Federal Register, vol. 62, No. 156 (Aug. 13, 1997) (10 pages).
Mayer, R. "Ignition interlocks—A toolkit for program administrators, policymakers, and stakeholders," 2nd Edition. Report No. DOT TH 811 883, Feb. 2014, Washington, D.C.: National Highway Traffic Safety Administration (60 pages).
Voyomotive, Llc, "What is Voyo?," Product description retrieved on Oct. 9, 2015 from http://voyomotive.com/what-is-voyo/ (4 pages).
"Non-Final Office Action," for U.S. Appl. No. 16/183,475 dated Sep. 22, 2020 (13 pages).

* cited by examiner

REFERENCE GAS MANAGEMENT IN A BREATH ALCOHOL CALIBRATION STATION

FIELD

The invention relates generally to breath alcohol device calibration, and more specifically to reference gas management in a breath alcohol calibration station.

BACKGROUND

Vehicles incorporate breath alcohol ignition interlock devices, sometimes abbreviated as BAIIDs, to prevent a driver from operating the vehicle while intoxicated with alcohol. Such devices are designed to prevent a driver from starting a motor vehicle when the driver's breath alcohol concentration (BAC) is at or above a set alcohol concentration. Each state in the U.S. has adopted a law providing for use of such BAIID devices as a sanction for drivers convicted of driving while intoxicated, or as a condition of restoring some driving privileges after such offenses.

In operation, a driver must use a BAIID device by blowing into a portion of the BAIID coupled to an alcohol-sensing element such as a fuel cell that measures the amount of alcohol in the driver's breath, thereby providing a reliable estimate of the blood alcohol concentration in the driver's blood. The BAIID reads a signal from the fuel cell or other alcohol-sensing element, and determines whether the driver's breath alcohol content exceeds a threshold amount. If the driver's blood alcohol content does not exceed the threshold, the driver is determined not to be intoxicated and the BAIID allows the vehicle to start and run by electrically enabling a system within the vehicle, such as the starter, fuel pump, ignition, or the like. If the breath sample delivered has a higher breath alcohol content than a predetermined allowable threshold, the vehicle is not allowed to start, and the BAIID device records a violation.

Repeated use of the BAIID device can contaminate the fuel cell or other alcohol sensing element, causing its sensitivity to ethanol in the user's breath to vary over time. To ensure that the BAIID measures alcohol accurately and consistently, regulations require that the BAIID be recalibrated from time to time, and that the BAIID be able to provide consistent results during and shortly after a stated recalibration interval.

A typical BAIID device meets guidelines established by the National Highway Traffic Safety Administration (NHTSA) in published model specifications for BAIIDs, which specify various tests that such a device must pass to make it an effective and reliable deterrent to intoxicated driving. For example, the model specifies tests designed to ensure a specified minimum volume of breath is delivered at a specified minimum flow rate against less than a specified maximum back pressure to ensure that an accurate result is produced, and specifies how such a device should be installed into a vehicle to prevent the vehicle from operating pending a determination that the driver is not intoxicated. The model also specifies that a device should be able to pass a calibration test within a specified tolerance for at least seven days past its stated recalibration period, which can vary from 30 to 90 days.

Recalibration typically involves recalibrating the BAIID device, or at least the portion of the device containing the fuel cell, in the vehicle or replacing it with a recently-calibrated device. If the BAIID is replaced, the removed device is then sent back to the manufacturer's calibration facility for recalibration, after which it is sent back to an installation or service center to be returned to service in another vehicle. The recalibration process involves using a reference gas having a known concentration of ethanol, such as compressed gas from a tank or gas generated using a wet bath solution. The reference gas is provided to the fuel cell or other alcohol sensing element, and the indicated output of the device is adjusted to correspond to the known ethanol concentration of the reference gas.

This ensures consistent and reliable calibration of the BAIID device, but because shipping the device from and to a service center and calibration can take a week or more, a high percentage of BAIID devices are constantly in transit to and from the manufacturer's service center. A need therefore exists for more efficient calibration of BAIID devices, while ensuring reliable and trackable calibration of the devices.

SUMMARY

In one example, a breath alcohol device calibration system includes a computerized calibration module operable to calibrate a candidate breath alcohol device using a reference gas of known alcohol concentration, and a reference gas tank identification module operable to identify a reference gas tank that is coupled to the breath alcohol device calibration system. Identification is performed using at least one distinguishing characteristic of the coupled tank, the distinguishing characteristic providing reference gas tank information including at least the known alcohol concentration of gas in the reference gas tank.

In a further example, the reference gas tank identification module is further operable to read a temperature history of the tank from an electronic device coupled to the tank, and to indicate an error condition if the temperature history of the tank indicates temperatures below a first temperature threshold over the tank's recent temperature history to potentially result in incomplete mixing of the reference gas.

In another example, a reference gas tank assembly for use in a breath alcohol device calibration system includes a reference gas tank operable to hold a reference gas under pressure greater than atmospheric pressure, and a machine-readable reference gas tank identification label affixed to the reference gas tank that is configured to indicate at least an alcohol concentration of a reference gas in the reference gas tank.

In a further example, the machine-readable reference gas tank identification label comprises at least one of an RFID (Radio Frequency Identification) label, barcode, NFC (Near Field Communication) label, QR code, or two-dimensional barcode attached to the reference gas tank.

The details of one or more examples of the invention are set forth in the accompanying drawings and the description below. Other features and advantages will be apparent from the description and drawings, and from the claims.

DETAILED DESCRIPTION

Figure 1:
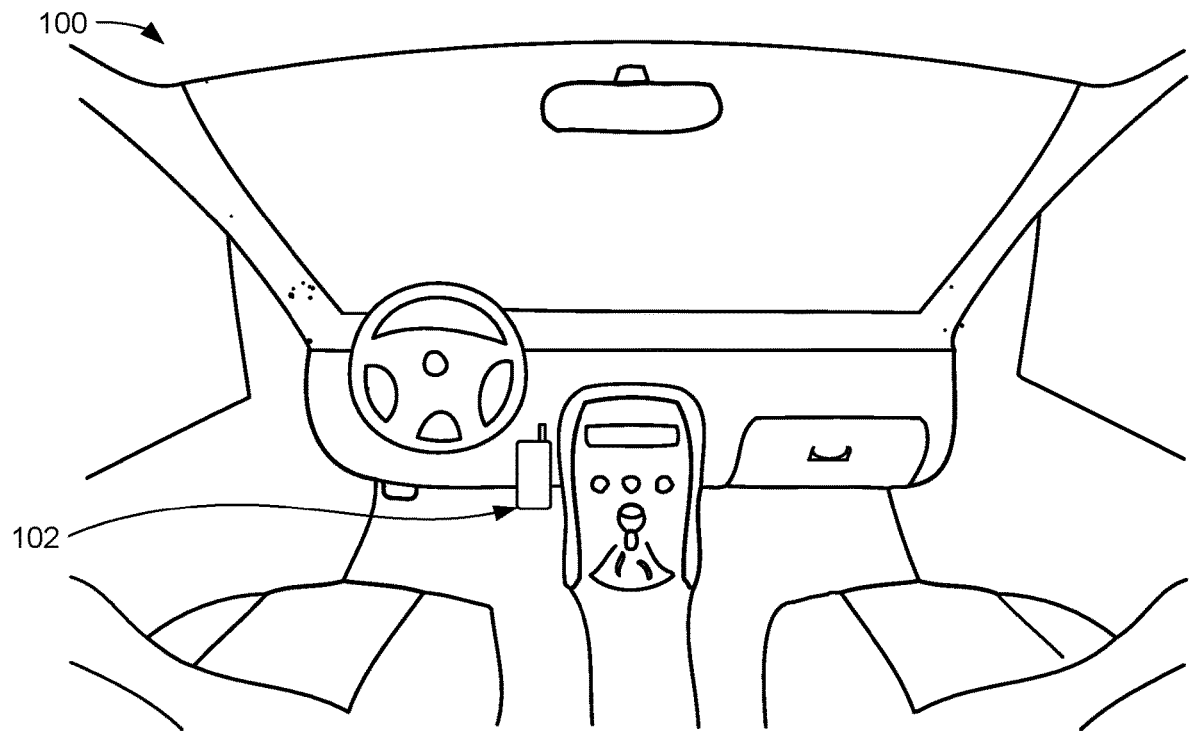
FIG. 1 shows a portion of an interior of a vehicle with a BAIID installed.

In the following detailed description of example embodiments, reference is made to specific example embodiments by way of drawings and illustrations. These examples are described in sufficient detail to enable those skilled in the art to practice what is described, and serve to illustrate how elements of these examples may be applied to various purposes or embodiments. Other embodiments exist, and logical, mechanical, electrical, and other changes may be made.

Features or limitations of various embodiments described herein, however important to the example embodiments in which they are incorporated, do not limit other embodiments, and any reference to the elements, operation, and application of the examples serve only to define these example embodiments. Features or elements shown in various examples described herein can be combined in ways other than shown in the examples, and any such combinations are explicitly contemplated to be within the scope of the examples presented here. The following detailed description does not, therefore, limit the scope of what is claimed.

Breath alcohol ignition interlock devices, also known as BAIIDs, are commonly installed in vehicles to prevent a driver with a history of driving while intoxicated from starting a motor vehicle when the driver's breath alcohol concentration (BAC) is at or above a set breath alcohol concentration. Concentration of alcohol in a driver's breath is closely proportional to the concentration of alcohol in the driver's blood, which is typically the basis upon which intoxication is legally determined. Because a driver must blow into a portion of the BAIID coupled to an alcohol-sensing element such as a fuel cell that measures the amount of alcohol in the driver's breath before the BAIID enables normal car operation, the BAIID can effectively prevent intoxicated drivers from driving a vehicle while intoxicated by selectively enabling the vehicle based on successful completion of the required BAIID test.

Proper operation of the BAIID device relies in part on its ability to accurately detect the amount of alcohol in a user's breath. NHTSA model specifications therefore stipulate that the BAIID device must be both accurate and repeatable in measuring breath alcohol, including specifying that a device having a threshold of 0.02 g/dL to start a vehicle will permit the vehicle to start 0.008 g/210 liters of breath but will not permit the vehicle to start at 0.032 g/210 liters of breath. Similarly, a BAIID must retain this ability for at least seven days past its recommended recalibration date, such as for 37 days for devices having a 30-day recalibration period. Certification of a new BAIID device therefore subjects a device to testing at 0.0 g/dL, 0.008 g/dL, and 0.032 g/dL at an initial test and at 37 days following the initial test. Manufacturers wishing to have longer recalibration intervals may further request that their devices be certified for longer intervals by also testing longer intervals of 67, 97, and 187 days. Because data is typically downloaded from a BAIID as part of the recalibration service, even BAIID devices that can remain within calibration specifications for 180 days may be subject to service intervals shorter than the certified calibration interval. This typically occurs when jurisdictions require vehicle inspections or data to be retrieved more frequently than the calibration service interval otherwise would allow. To ensure correct calibration and regular downloading of data, BAIID devices will lock a user out from operating the BAIID or associated vehicle seven days after the programmed service interval.

Servicing a BAIID device typically involves either calibrating the BAIID device in the vehicle, or removing the BAIID device (or at least a portion of the device containing the ethanol measurement element) from the vehicle and replacing it with a recalibrated BAIID device. If the BAIID device is removed for recalibration, the removed device is packaged and returned to the manufacturer, where the manufacturer downloads data such as successful tests and vehicle starts, tampering attempts, and unsuccessful tests, and recalibrates the alcohol sensor in the device. Recalibration involves introduction of a reference gas having a known concentration of ethanol, such as using a wet bath or a compressed dry gas assembly, and programming the removed device to ensure that the proper breath alcohol concentration is displayed for the reference gas.

The expense of shipping BAIID devices between installers and a calibration facility is substantial, and the relatively short recalibration period of 30 days and shipping and calibration time of 7-10 days means that a substantial number of BAIID devices in circulation are always out of service for shipping and calibration. Having several calibration facilities may reduce mailing times, but imposes challenges such as ensuring accuracy of calibration and ensuring security and integrity of data across multiple calibration sites.

Some examples described herein therefore provide for BAIID calibration incorporating features such as secure data management and improved reference gas tank management in a calibration station that can be used at an installation site, thereby eliminating the need to send a BAIID device back to the manufacturer or other central location for calibration and data retrieval. In one such example, the BAIID calibration station includes an interface operable to couple the breath alcohol device being calibrated to a remote server using a connection employing a cryptographic function such that data stored on the breath alcohol device can be securely downloaded from the breath alcohol device to the remote server. This reduces the likelihood of a calibration station technician or other user from reading or tampering with the data before it is downloaded, or from downloading false data to the remote server. In another example, reference gas is automatically identified using a reference gas tank identification module, which is operable to identify a reference gas tank that is coupled to the breath alcohol device calibration system using at least one distinguishing characteristic of the coupled tank. The distinguishing characteristic is a feature associated with reference gas tank information. One example of a distinguishing characteristic is the actual alcohol concentration of gas in the reference gas tank, determined by the manufacturer or provider of the reference gas. Other examples of distinguishing characteristics are the labeled alcohol concentration of gas in the tank, the labeled pressure of the gas in the tank, the volume of the tank, the manufacturer of the reference gas tank, and a manufacturer's serial number or other identification number of the reference gas tank.

FIG. 1 shows a portion of an interior of a vehicle with a BAIID installed. Here, the interior of a car 100 includes a driver's seat on the left, a front passenger seat on the right, a steering wheel, and other common elements of a typical car interior. The vehicle further includes an installed BAIID 102, which is configured to interact with the vehicle in such a way that it is operable to allow the vehicle to start or run only if certain conditions are met. This is achieved in some examples by wiring the BAIID directly to vehicle systems such as the starter, ignition, fuel pump, or the like, and in other examples by communicating with vehicle systems through the On-Board Diagnostic (OBDII) connector, a replacement wireless relay, or through other such mechanisms.

In operation the user of a vehicle having a BAIID installed must provide a breath sample meeting certain requirements for volume, temperature, and other such characteristics to the BAIID device 102, so that the breath sample can be tested for ethanol concentration before allowing the vehicle to start. If the user's breath alcohol exceeds a predetermined threshold, the vehicle will not start and will register an unsuccessful start attempt or a violation. If the user's breath alcohol is below the threshold and the BAIID allows the vehicle to start, the BAIID will require periodic retests while the vehicle is in operation, reducing the likelihood that the breath provided to start the car was provided by another party and that the driver has not started drinking while driving. Various additional security measures often include cameras to record images the cabin of the vehicle including the driver's and passenger areas, providing the breath used for each test, and systems designed to detect tampering with the vehicle or BAIID such as attempts to start the car when no valid test has been performed.

Figure 2:
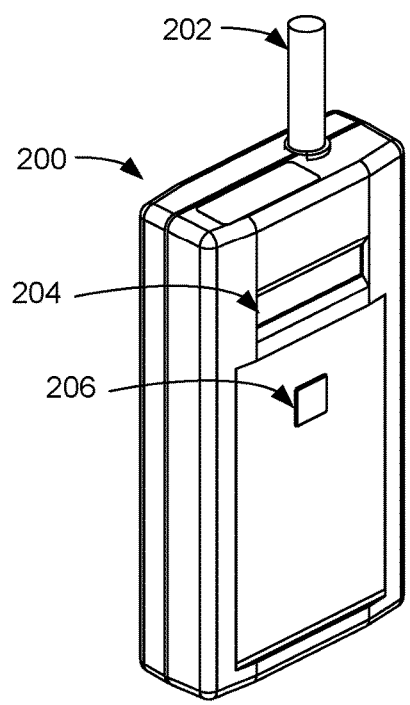
FIG. 2 shows an example BAIID handheld.

FIG. 2 shows an example BAIID handheld. The handheld 200 in various examples operates in conjunction with other components, such as a relay box, external camera, or other components. Here, the handheld 200 includes a replaceable breath tube 202, a display 204, and other features not shown such as a fuel cell element operable to detect the ethanol concentration in a user's breath sample delivered through replaceable mouthpiece 202. The display 204 indicates the state of the BAIID, and provides information to the user regarding testing, retesting, and various other instructions. A button 206 is further provided to receive user input in the handheld, while in other examples more buttons are provided or the display 204 is a touchscreen, providing for greater user interaction with the handheld.

Figure 3:
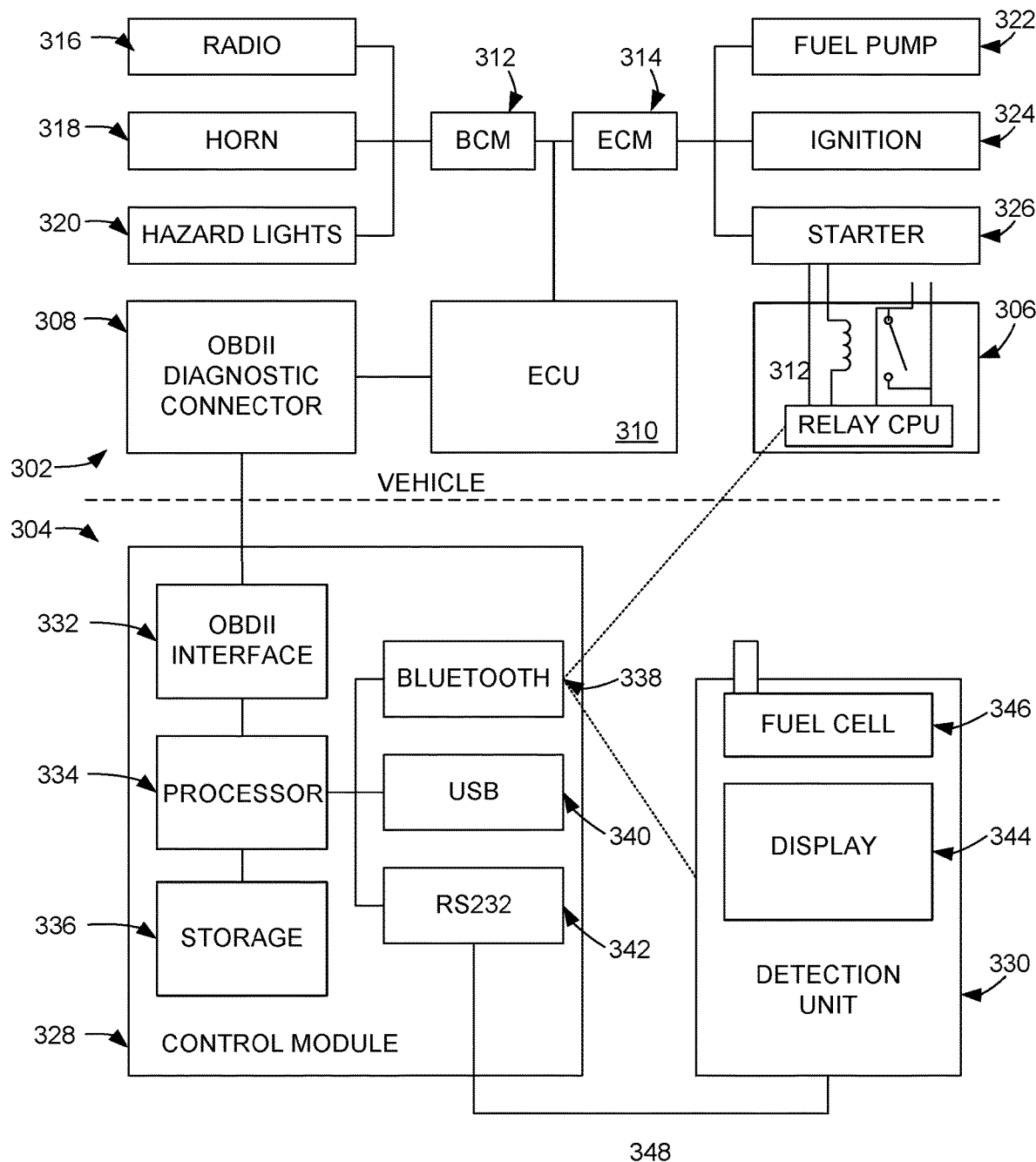
FIG. 3 shows an example ignition interlock system coupled to a vehicle.

FIG. 3 shows an example BAIID coupled to a vehicle. In this example, vehicle electrical system elements shown at 302 are coupled to elements of the BAIID system 304, such as through an OBDII diagnostic connector 308, Bluetooth or other wireless connections 338, or traditional direct-wired connections. The BAIID system includes a control module 328 that provide processing, communication, and control functions, and a handheld detection unit 330 that includes a fuel cell 346 or other alcohol detection element. In some examples, elements of the detection unit and control module are integrated into the same device, such as a standalone handheld device, or a smartphone with a fuel cell attachment.

In operation, the control module 328 prevents one or more vehicle systems 302 from functioning until a breath alcohol test has been successfully completed, such as by blowing into the BAIID when prompted. The control module determines whether the breath sample is valid and contains measures the breath alcohol concentration, and controls the vehicle systems through one or more connections to selectively enable the vehicle system in response to the test result.

Figure 4:
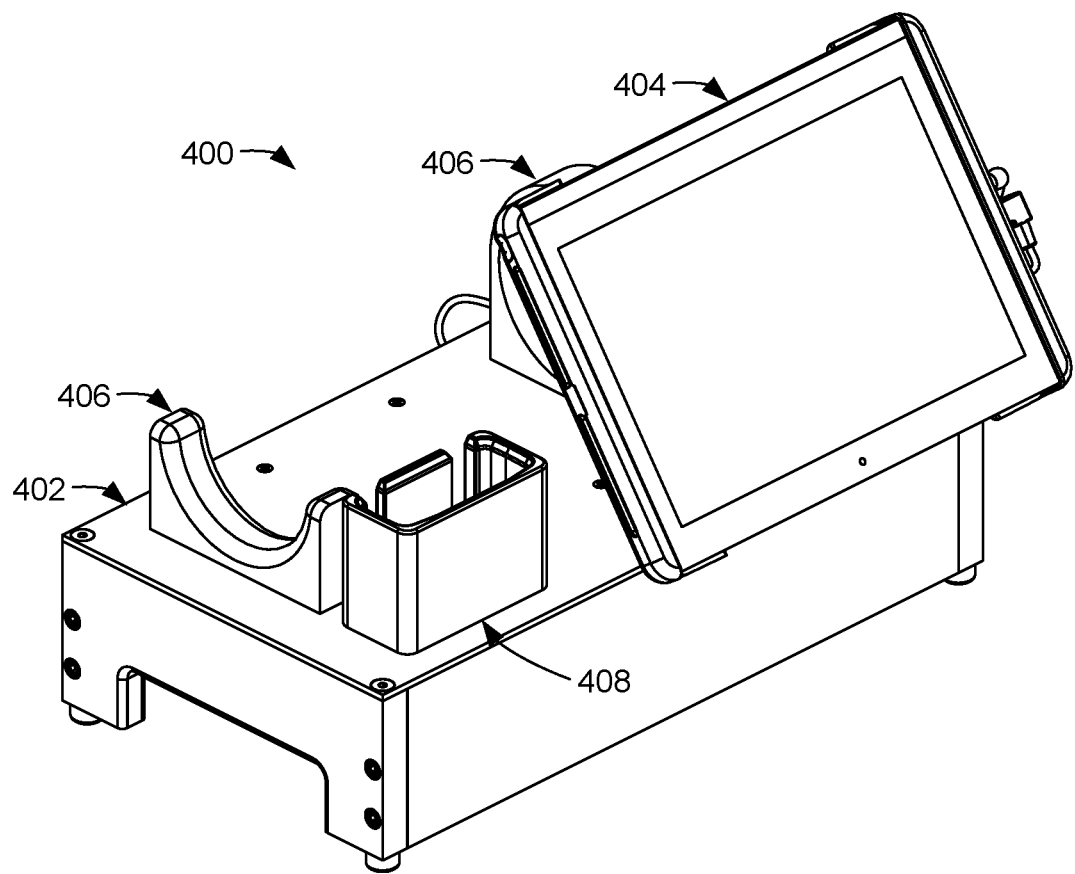
FIG. 4 shows a calibration station, as may be used to calibrate the BAIID devices of FIGS. 2 and 3.

FIG. 4 shows a calibration station 400, as may be used to calibrate the BAIID devices of FIGS. 2 and 3. The example calibration station 400 is portable, such that it can be readily be moved by a single person and shipped via common carriers. The calibration station primary components include a base 402 upon which other components are mounted, as well as a tablet computer that serves as a controller 404. A reference gas tank is held by tank mount 406, such that tanks of reference gas can be cradled in the tank mount and threaded onto a receptacle comprising part of the calibration station. The receptacle is further coupled to an electrically-actuated valve, such that the controller 404 is operable to open and close the valve to control flow of reference gas from the reference gas tank.

A BAIID cradle 408 is also provided, and includes a sealed gas interface to the BAIID's fuel cell 346 of FIG. 3, through the sampling port of the BAIID (not depicted in figure) The gas interface is sealed during the calibration process to prevent leakage or infiltration of outside air or other contaminants that could affect accuracy of the calibration. The controller 404 is operable to control the flow of reference gas from the reference gas tank to the BAIID via the gas interface, thereby delivering reference gas to the BAIID mounted in the BAIID cradle 408 only during calibration.

Figure 5:
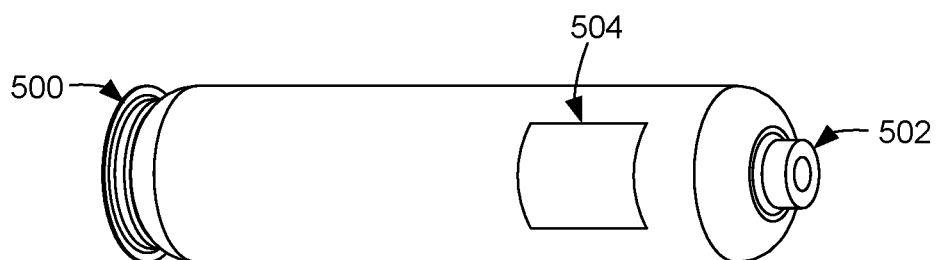
FIG. 5 shows a reference gas tank, as may be used with the calibration station of FIG. 4.

FIG. 5 shows a reference gas tank, as may be used with the calibration station of FIG. 4. The reference gas tank 500 is a cylinder designed to hold a compressed gas mixture, which includes a reference amount of ethanol for use in calibrating a BAIID device. The reference gas tank includes a threaded valve portion 502, which is operable accept the receptacle on the calibration station 500, and to prevent flow of gas from the reference gas tank until it is connected to a receptacle.

Because reference gases are provided with various ethanol concentrations, the calibration station 400 needs to either work with a specified concentration of ethanol in the reference gas or to be programmed with the concentration of ethanol in the reference gas to provide accurate calibration. In previous examples, this was achieved by typing in a reference gas concentration, or by reading a reference gas indication such as a barcode from a paper or certificate provided with the reference gas tank. Methods such as these are prone to error, particularly in environments in which different reference gas concentrations are used for different manufacturer's products or for other purposes.

In some examples, the calibration station is structured so that a distinguishing characteristic of a reference gas tank is automatically identified using a reference gas tank identification module while the reference gas tank is coupled to the breath alcohol device calibration system. In some examples, the identification module is operable to identify the reference gas tank during the process of attaching the reference gas tank to the calibration station, such as optically scanning a code while the tank is rotated into a coupled position. In some examples, the identification module is not operable to identify or automatically identify the reference gas tank unless the tank is attached to the calibration station.

One solution is to integrate a breath alcohol sensor such as a fuel cell or other measurement device into the calibration station 400, such that the reference gas can be measured and determined to be within an allowable range from the labeled and expected reference gas ethanol concentration before calibration is performed whenever a new reference gas tank is detected. In some examples, an internal breath alcohol sensor is contained within the base 402 of the calibration station 400 shown in FIG. 4. For example, a reference gas that is labeled as and expected to have a reference alcohol concentration of 0.050 grams per 210 liters of ethanol may be acceptable if a calibration station's internal fuel cell determines the reference gas is 0.050±0.003 grams per 210 liters. In a more sophisticated example some drift of the internal sensor is allowed over time, such that a correction of a first percentage of error may be acceptable if history shows a drift in the detected reference gas concentration over time toward that first percentage of error, but the same first percentage of error may be deemed unacceptable if there is a sudden change in the percentage of error of the detected reference gas. In one such example, a 4% cumulative correction may be acceptable if history shows a steady drift in calibration over time, such as from a −1% to 3% correction factor over time, but a 4% correction may fail if the detected percentage changes by 7% from recent prior readings to be off by 4% from the expected value, such as from a −4% to +3% correction factor in subsequent calibrations. Solutions involving a fuel cell or other measuring element in the calibration station are less desirable in some applications because they are expensive. A fuel cell based gas measurement system can account for approximately ¼ the cost of such a calibration station. Tolerances permitted may vary by jurisdiction or by device model, such as 0.5%, 1%, 2%, 3%, or 5% variation from the anticipated ethanol concentration.

The example reference gas tank shown in FIG. 5 incorporates a label 504 that the calibration station 400 can read when the reference gas tank is mounted in the reference gas tank cradle 406, such as by using optical or radio sensors to read the label 504. The label 504 includes a barcode, RFID (Radio Frequency Identification) tag, or other machine-readable element incorporated into label 504 such that the calibration station can read the element when the reference gas tank is installed in the calibration station.

In one example, this is achieved by using a camera on tablet computer controller 404 to visually read the tag as the tank is installed into the calibration station or after than tank is installed into the calibration station. In another example, the tank mounting cradle 406 includes a radio frequency antenna configured to read an RF tag such as an RFID or NFC (Near-Field Communication), an optical scanner configured to read an optical tag such as barcode, QR tag, two-dimensional barcode, shotgun or scattergram pattern, or is otherwise configured to sense the element of label 504 that indicates the reference gas concentration of the tank. Tracking individual reference gas tanks also permits more accurate characterization of the reference gas on a tank-by-tank basis, such as indicating that a reference tank of 0.050 grams ethanol per 210 liters balance gas nominal is actually provided as 0.0502 grams ethanol per 210 liters balance gas.

The tank shown in the example of FIG. 5 is a 105 liter tank, which holds 105 liters of gas when compressed to 1000 psi. This is enough gas to perform approximately 180-300 calibration cycles in one example calibration station, enabling many weeks of operation without changing the reference gas tank. The label 504 in various examples indicates the volume of the tank, one or more constituent gases and percentages in the tank, information providing traceability or documentation of the reference standard gas in the tank such as lot or batch number, and other such parameters as may be useful in using the reference gas to perform BAIID calibrations. The label in some examples indicates this information through being directly encoded on the label, while in other examples the label comprises a reference number or other identifier that is associated with the reference gas information, such as through a secure database. In some examples, the label includes all or some of this information as human-readable text.

Because solutions such as these read the label affixed to the tank, it is not necessary for a user of the calibration station to input information into the calibration station. This reduces the risk of errors. This approach also reduces the risk that a user can intentionally deceive the machine into believing a reference gas contains more ethanol than it actually does. Without such safeguards, it would be easier for a service center technician to intentionally provide a higher ethanol concentration reference gas, such as 0.100 grams per 210 liters reference gas, for calibration while indicating to the machine that a lower reference gas, such as a 0.050 grams per 210 liters reference gas, was being used, thereby resulting in an inaccurate BAIID calibration, such as one allowing twice the breath alcohol as permitted by regulations in breath alcohol tests. For reasons such as this, the label 504 is in some examples is made to be difficult to remove from the tank without destroying the label, such as by using a strong adhesive or band around the tank to affix the label to the tank.

Under certain circumstances, the temperature history of a reference gas tank can result in the output of certain component gases from that tank being higher or lower than the label indicates. If the temperature of a reference gas tank containing ethanol and nitrogen dips below the dew point of ethanol, part of the ethanol in the tank returns to the liquid state and condenses on the cylinder walls. The dew point of ethanol increases with increasing pressure and thus is more problematic in highly pressurized containers. If gas is released from the tank while part of the ethanol is condensed on the cylinder walls, then the accuracy of the mix in the tank will be forever altered and cannot be readily restored. As the temperature of the tank rises again after a dip below the dew point, the condensed ethanol will return to a gaseous state. After minor drops below the dew point, it is likely that the gas in the tank will remix by diffusion over a short period of time without any special steps, so that the gas released will be accurate to its labeled concentration. If a more significant temperature drop occurred, then a longer passage of time such as 24 hours, or rolling the warmed tank, will remix the tank so that the gas released will be accurate to its labeled constituent component concentration.

In a further example, the label 504 or other component of the reference gas tank is operable to track tank temperature over time, such as by recording periodic temperature measurements via a device thermally coupled to the body of the tank or cylinder and storing them electronically in a manner that can be conveyed to another device, such as through an RFID tag or NFC tag. The calibration station can use temperature history to reduce the risk that the reference gas tank is opened when the recent tank temperature has been low enough for ethanol to condense on the cylinder walls. The calibration station can also use temperature history to look for the possibility that the tank was opened when the tank temperature was low enough for ethanol to condense on the cylinder walls. These steps are used to check whether the ethanol percentage in reference gas released for the calibration process is at risk of being inaccurate.

In a more detailed example, a critical temperature is determined below which a component of the reference gas condenses out of the gas solution. The critical temperature varies based on the concentration of the gas solution and the tank pressure. The calibration station can be programmed not to open the valve connected to the tank until the tank temperature has been above the critical temperature for a sufficiently long time for any condensed ethanol to re-evaporate into the gas mixture. In further examples, other safeguards such as measuring pressure of a new gas tank to verify that the tank has not been opened and measuring the ethanol concentration using a reference fuel cell in calibration station or in the BAIID under calibration to verify that the reference gas is close to the indicated ethanol concentration are employed.

In an alternate example, the calibration station 400 includes a mechanism for measuring the temperature of an installed tank, such as an infrared pyrometer. This enables the calibration station to monitor the temperature of the reference gas tank 500 as well as the tank's change in temperature over time, enabling the calibration station to determine whether the tank temperature is both sufficiently warm and sufficiently stable to indicate that any precipitated ethanol will be re-evaporated into the gas mixture. In a more detailed example, a calibration station controller calculates whether the tank temperature is both well above a warm temperature threshold at which compressed ethanol condenses and is sufficiently stable in temperature to indicate complete mixing of the reference gas.

Figure 6A:
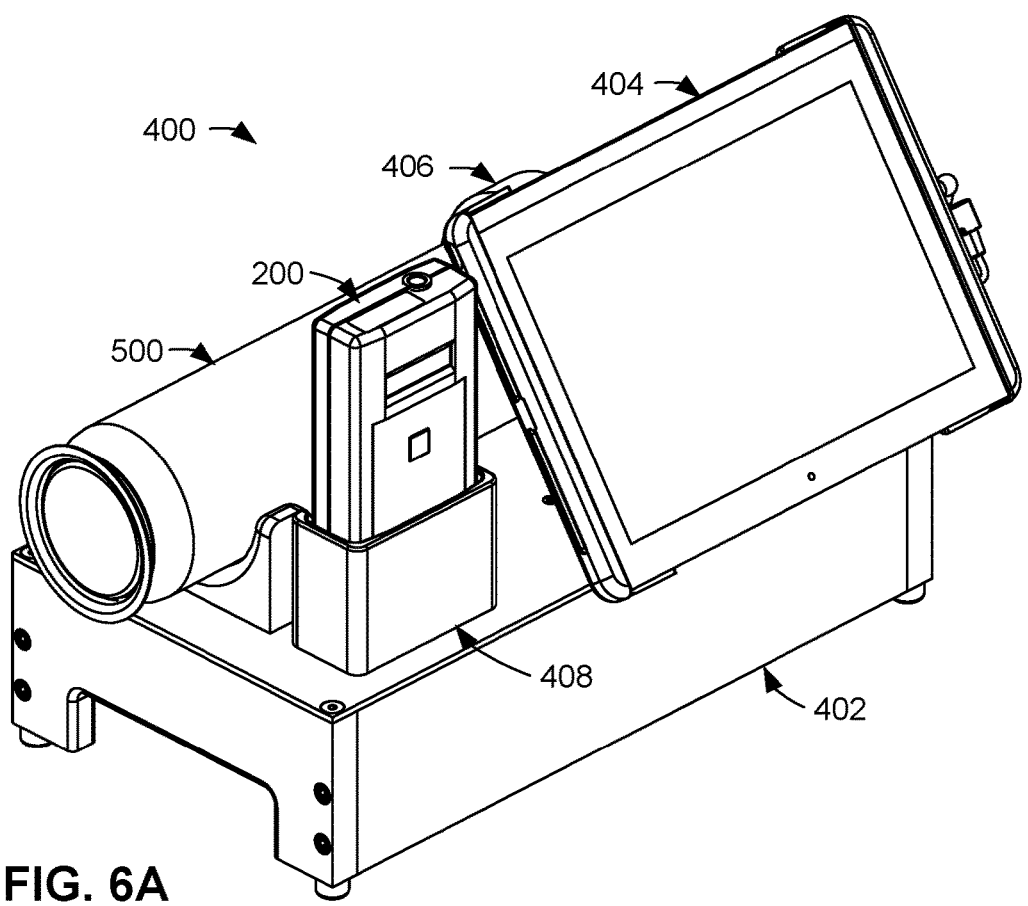
FIG. 6A shows a calibration station with a BAIID and reference gas tank installed.

FIG. 6A shows a calibration station with a BAIID and reference gas tank installed. Here, the calibration station 400 includes an installed reference gas tank 500, which is read by an RF or optical reader in tank cradle 406 or by a similar element in tablet computer controller 404 during or after installation. The calibration station also includes a BAIID cradle 408 that is electrically coupled to the BAIID device 200 such that the calibration station can read electronic data from the BAIID. The calibration station further is fluidly coupled to the BAIID's fuel cell, such as by providing gas to a gas port on BAIID 200 such as at the bottom of the BAIID when inserted into cradle 408 to securely provide the reference gas to the BAIID's fuel cell for calibration. In other examples, the calibration station is coupled to the BAIID by providing a coupling in place of the replaceable mouthpiece.

The assembled calibration station in this example also has various internal components, including a power supply for powering the tablet computer controller 404 and the BAIID 200. The calibration station further includes a networking element, such as a WiFi, cellular data, Ethernet, or other network connection enabling the calibration station to send data to a central server.

Figure 6B:
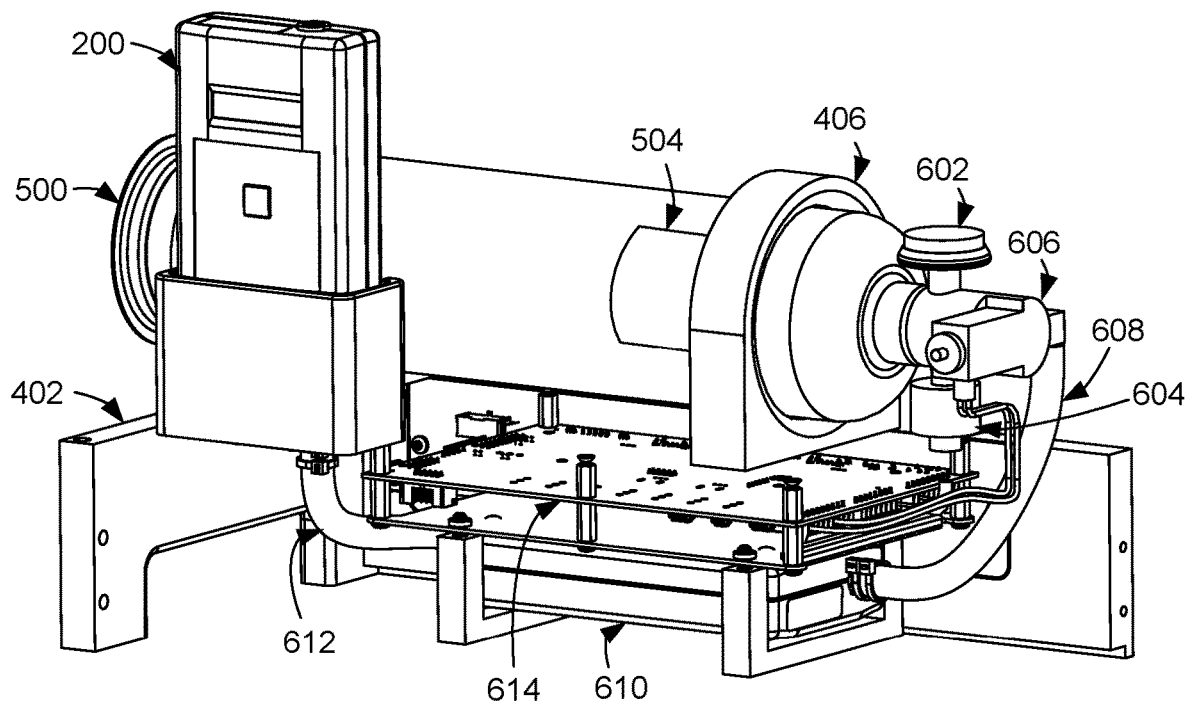
FIG. 6B shows a calibration station with a BAIID and reference gas tank installed and chassis panels removed.

FIG. 6B shows a calibration station with a BAIID and reference gas tank installed and panel of chassis 402 (shown in FIGS. 4 and 6A) panels removed. Here, the handheld 200 and reference gas tank 500 remain installed in the chassis 402, and the label 504 is in position to be read by a sensor such as on gas tank cradle 406. The reference gas tank 500 is coupled to a pressure gauge 602 and an electronic pressure transducer 604, which indicate the pressure of the reference gas tank and indirectly indicate the amount of gas remaining in the tank. A pressure regulator and valve 606 reduce the tank pressure to a working pressure, such as 50 psi from the regulator which is then further reduced to near atmospheric pressure by an orifice in the valve, and a hose 608 connects the regulated gas to an internal breath alcohol analyzer 610 that is operable to ensure the reference gas is at or near the expected ethanol concentration. The internal breath alcohol analyzer is further connected by hose 612 to the BAIID 200's cradle, such that reference gas mixture flowing through the internal breath alcohol analyzer 610 is provided to the BAIID 200 for calibration. A car simulation board 614 is also included in the calibration station to simulate various automotive functions, such as lights, horn, fuel pump, starter motor, and other systems with which the BAIID 200 interacts.

In operation, the tank pressure transducer 604 allows the controller to prompt a technician for cylinder replacement if the tank pressure drops below a predetermined pressure such as 50 psi, while the regulator and valve assembly 606 maintains a nearly constant flow of gas to the BAIID at atmospheric pressure. The pressure monitor in a further example is operable to detect significant changes in pressure or pressures beyond certain thresholds, such as detecting an overfilled tank, or detecting a drop to zero pressure indicating that a tank has been removed.

The calibration station also includes certain sensors that are not shown, and that are used to ensure the environment for calibration is appropriate, or to compensate for environmental variation. A pressure sensor in one example measures atmospheric pressure so that the controller can adjust the concentration of the reference gas as appropriate to compensate for altitude or other pressure variations. The calibration station is calibrated to be accurate at sea level, but the concentration of ethanol provided by the reference gas cylinder decreases by about 3% for each 1000 feet of altitude above sea level (or equivalent above a standard pressure of 29.92 inches of mercury), so the controller uses the measured atmospheric pressure to compensate for such pressure variations. Ssimilarly, the calibration station includes a thermometer that measures ambient temperature, enabling compensation for an approximate 0.3% decrease in ethanol concentration for each degree above 34 degrees Celsius, This is the industry agreed-upon temperature of human exhaled breath and the temperature at which the gas concentration stated in weight/volume terms on the reference gas cylinder is accurate. At temperatures below 34 C, heaters on the fuel cell of the BAIID keep the fuel cell at 34 C. The gas temperature increases to 34 C when it contacts the surface of the fuel cell which is thermally massive compared to the breath sample introduced to the fuel cell. Thus no adjustment of the reference gas to compensate for temperature is required at ambient temperatures at or below 34 C.

The calibration station also includes an electronic data connection to the BAIID 200, enabling the calibration station to retrieve data such as user history and error messages from the BAIID. For example, a device being submitted for calibration after a 30 day service interval will have approximately 30 days of recorded user successful tests, vehicle starts, failed tests, and other such information stored in the BAIID Errors such as unauthorized starting attempts, disconnection from one or more vehicle systems, and other problems are also recorded. This information is important to verify that the BAIID has been operating correctly in the user's vehicle and in the calibration station, and that the user has remained in compliance with the terms under which the BAIID is provided.

The stored data is therefore uploaded from the BAIID to a central server or other authority for review, and is secured and conveyed in a way that discourages altering or interfering with the data that is uploaded. In some examples, the calibration station of FIG. 6 is designed to be relatively inexpensive and easy to transport, so that installers can have their own on-site calibration stations. Installers and service centers with their own calibration stations at their installation facilities do not need to send BAIID components to the manufacturer's central location for calibration or data upload. Although the calibration stations are not designed for operation by the BAIID user, BAIID data handled by the calibration station is secured in part because a temptation remains for an installation center employee to alter data such as unsuccessful breath tests before the data is uploaded to the central server, such as in exchange for cash from the BAIID user. Privacy of the BAIID user data can also be enhanced with secure connections and other data handling steps.

In one example calibration station configuration, the tablet computer controller 404 is coupled to a USB port on the calibration station's chassis 402. The controller performs functions such as retrieving stored data from the BAIID 200 being calibrated, and communication with the central server via WiFi, wired network, cellular data network, or other suitable connection to upload data from the BAIID In a more detailed example, an application on the controller retrieves data from the BAIID that is encoded in a format that is not readily human-readable, and sends the data directly to the central server using a secure connection such as SSL (Secure Socket Layer) or TLS (Transport Layer Security) encryption to ensure the integrity of the data. In this example, no data is stored in the controller other than in memory, such as volatile memory, while the data is being retrieved from the BAIID and uploaded to the central server. In a further example, data is erased from volatile and/or nonvolatile storage on the calibration station controller once the central server has confirmed receipt and storage of the data. The connection between the controller and the BAIID is also secured in a further example, such as to reduce the chances of alteration of data exchanged between the BAIID and controller.

A cryptographic function is a technique used to ensure the integrity of data, such as encoding data in a format that only authorized recipients can read or marking data with a signature or hash function such that alterations are evident. The goal of a cryptographic function is to make the data more resistant to being tampered with if it is intercepted by someone who is not intended to receive it. Although SSL certificates are used to encrypt and decrypt the data transferred between the calibration station and the central server in this example, other examples will use hash functions, public or private key encryption, elliptic curve encryption, digital signatures, cryptographic authentication, cryptographic identification, and other such cryptographic technology to verify that the data being exchanged is authentic and has not been altered.

To perform a calibration that includes data upload, a user inserts the BAIID 200 into cradle 408, and launches a calibration application using controller 404. The controller identifies the presence of the handheld using the USB connection to the chassis 402 and the BAIID's electrical connection to the chassis, and begins to download data from the BAIID and to send the downloaded data to the central server using the secure SSL connection. The controller 404 also downloads data from the central server regarding the BAIID, including user settings, calibration settings, state rules, reference gas information (in some embodiments), and other such information. After the data transfers are complete, the server confirms proper receipt and storage of the received data, and provides a signal indicating that the controller may now proceed to calibrate the specific, identified BAIID in the cradle 408. The calibration station's controller then begins the calibration function, which in a more detailed example comprises installing special calibration mode firmware on the BAIID and executing the calibration firmware. Once calibration is complete, the calibration parameters are stored in the BAIID. Next, firmware configured for normal operation of the BAIID is installed on the BAIID. In a further example, the new firmware comprises information specific to the jurisdiction in which the BAIID will be used, such as acceptable tolerances, retest rates, and other parameters. In another example, the firmware includes installing customer profile information that may modify operation of the BAIID, such as for a user who has a reduced lung capacity and may only be able to provide a limited continuous breath sample. Because functional firmware is loaded onto the BAIID only after calibration is successfully completed, the BAIID cannot be removed and installed in a vehicle between the time when the data upload and calibration process is started and the time the process is completed.

The controller 404 is "hardened" in some examples, meaning that the controller is limited in functionality to reduce the ability of installers or technicians to perform unauthorized functions. For example, the controller in this example executes a Windows operating system, but does not provide a web browser, a control-alt-delete function, ability to install new applications, or other standard Windows functionality to an installer or technician. Data downloaded from the BAIID and uploaded to the central server is also not provided to or exposed to the technician performing the calibration, further reducing the temptation and ability to alter the data and increasing BAIID user privacy. In another example, data stored on the handheld BAIID 200 is obfuscated or encoded such that the data is not presented in human-readable form such as the English language, and its meaning is not readily apparent to a human reader.

Uploaded data may vary by jurisdiction, BAIID model, or for other reasons, but in this example includes one or more of user history, vehicle starts and corresponding breath alcohol, raw sensor data (uncalibrated or uncompensated), temperature, unsuccessful vehicle starts and corresponding breath alcohol, unauthorized vehicle starts, detected invalid states such as vehicle running without completion of a valid test, and other such data. The event data is typically associated with a time stamp. Malfunctions, diagnostic logs, and other such information may be included and used by the BAIID, the controller, or the central server to indicate that a BAIID should be sent for service when it is brought in for calibration.

Although the calibration station uploads data from the BAIID to the central server in this example, the BAIIDs in other examples will include cellular radios or other means for uploading data, such that data upload need not be part of the calibration process. Calibration periods of 30-60 days are common in the industry, in part to ensure that data from the BAIID is uploaded at least once or twice a month and that the user's vehicle is inspected periodically for signs of tampering or circumvention Because many BAIID devices can hold their calibrations within acceptable tolerances for 180 days or more, calibration periods can be significantly lengthened in environments where the BAIID can self-report data without being brought in to a service or installation center, such as when the BAIID incorporates a cellular radio, is integrated into a smartphone, or includes other such communication capability.

Figure 7:
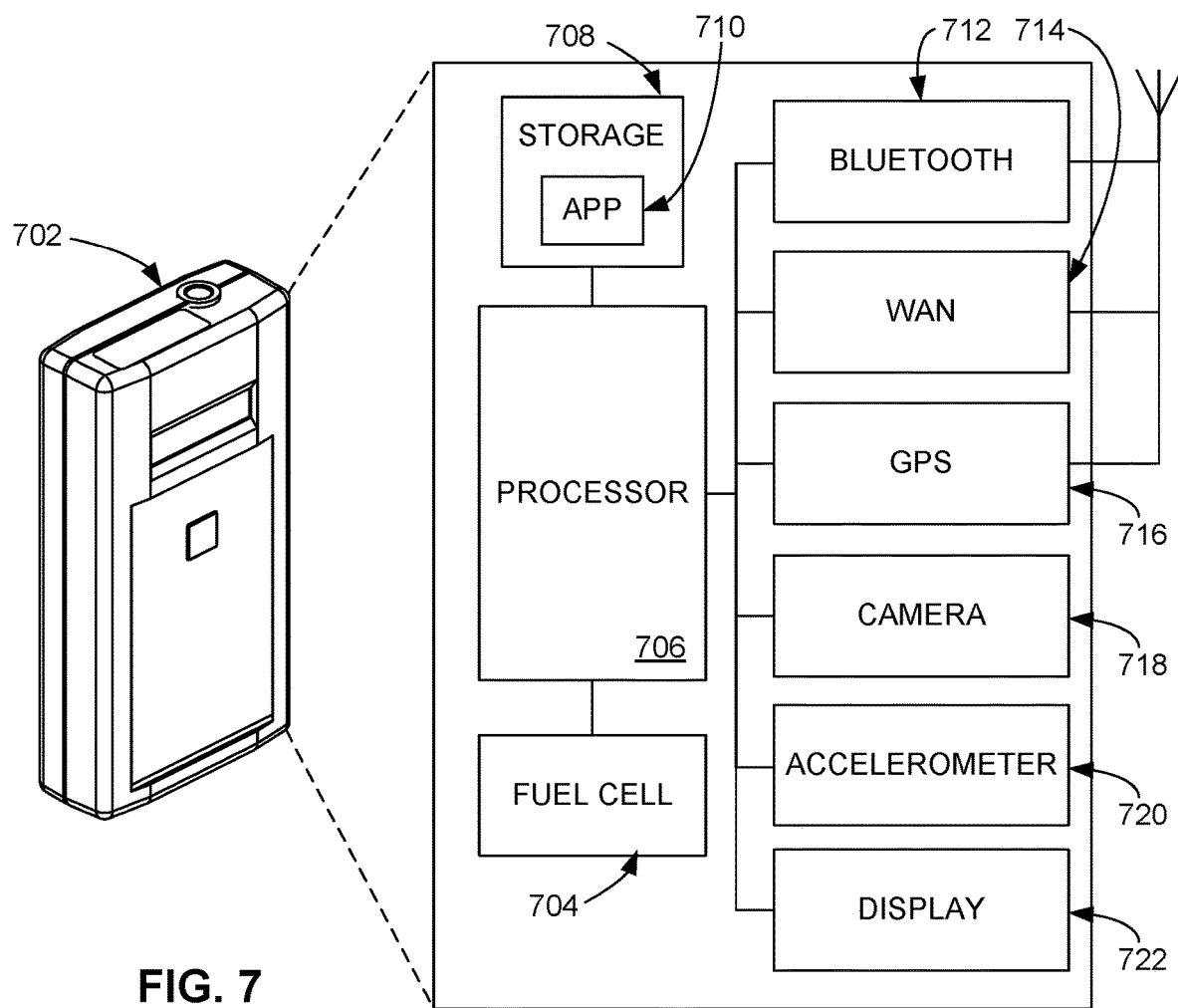
FIG. 7 shows a control module for a breath alcohol ignition interlock system, including a wide-area network radio such as a cellular data radio.

FIG. 7 shows a handheld control module for a breath alcohol ignition interlock system. Unlike the example shown in FIG. 3, the handheld of FIG. 7 includes various control module features and a wide-area network radio such as a cellular data radio. Here, the handheld BAIID housing 702 includes fuel cell 704 or other device operable to detect intoxication in a user's breath. The BAIID handheld also comprises a processor 706, and storage 708 which stores application software 710 that is operable to perform at least some functions of the BAIID system. The software 710 interacts with other elements of the BAIID, such as the BAIID's Bluetooth radio 712, cellular radio or wide-area network (WAN) 714, global positioning system or GPS 716, camera 718, accelerometer 720, and display 722.

As with the examples of FIG. 3, the Bluetooth radio 712 can be used to communicate with a Bluetooth relay, with an OBDII wireless interface, or with other components of the BAIID system. The cellular or WAN connection 714 may again be used to communicate information from the controller to a remote monitor or remote server, such as to transmit violation records or images of users while taking intoxication tests to verify identity. Similarly the GPS 716 may be used to verify or track the location of the vehicle, and may further be used in conjunction with or as an option to accelerometer 720 to ensure that the vehicle is not moving until a valid intoxication interlock test has been completed. Camera 718 can capture images of the person taking an intoxication test, such that the images are recorded or are transmitted such as via the cellular radio to monitor that the correct person is taking the intoxication tests. Because the handheld BAIID 702 contains functions of both the handheld and the controller of FIG. 3, it provides for easier installation and operation than such examples made up of separate units.

Figure 8:
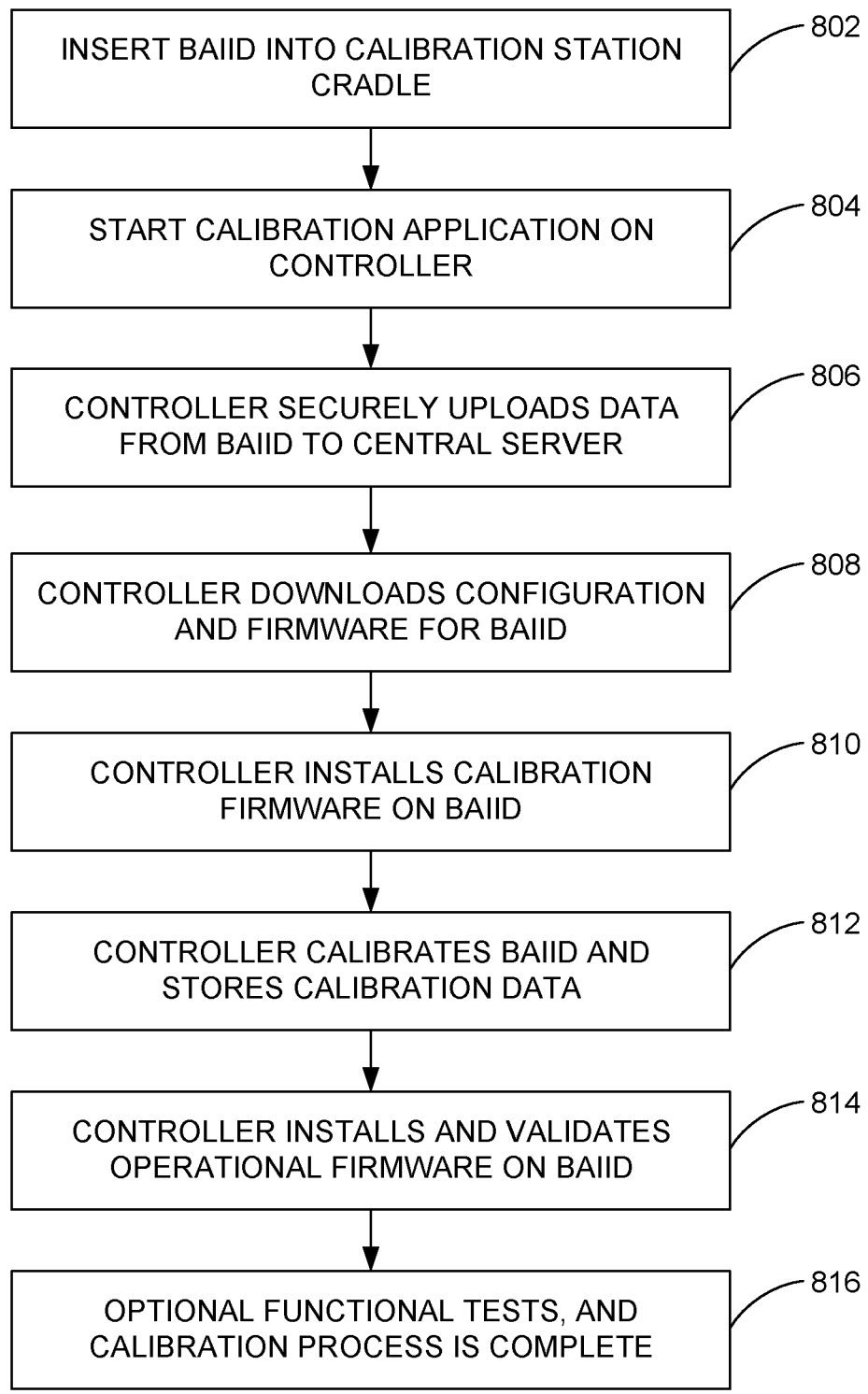
FIG. 8 is a flowchart illustrating an example method of calibrating a BAIID using a calibration station.

FIG. 8 is a flowchart illustrating an example method of calibrating a BAIID using a calibration station. At 802, the BAIID is removed from the user's vehicle and installed into the cradle of the calibration station. The calibration station is also powered and has a cylinder of reference gas installed for calibration. An installed calibration station will only need reference gas changed after approximately 300 calibrations. The BAIID is inserted in the cradle in a manner that provides both electrical communication with the calibration station and a sealed fluid connection between the calibration station and the BAIID's alcohol sensor, such as a fuel cell. The calibration station's controller starts the calibration application at 804, such as in response to user input or in response to detecting the presence of a newly-attached BAIID. At 806, the controller pulls data from the BAIID, including diagnostic information, use history, and other such data, and securely uploads it to a central server. In a more detailed example, the secure upload comprises use of SSL or other encryption, to ensure the integrity of the uploaded data. When the connection between the central server and the controller is established, the controller also downloads configuration information for the specific BAIID at 808, and downloads firmware and other configuration information such as jurisdictional configuration rules for calibration and for operation of the specific BAIID device.

Once the data exchange is complete, the calibration station's controller installs calibration-specific firmware on the BAIID at 810. The calibration-specific firmware does not operate the BAIID in a normal mode that would be used to verify breath alcohol before starting a vehicle, but instead performs functions specific to calibrating the BAIID's ethanol-sensing element. In an alternate example, the calibration and operational firmware are combined, and a calibration mode is initiated by the controller. At 812, the controller sends instructions to the BAIID to perform calibration functions, while also controlling other components of the calibration station such as the valve controlling the flow of gas from the reference gas tank to the BAIID under test. As part of the test, either the controller or the BAIID calculates the difference between the level of ethanol in the reference gas provided and the level of ethanol indicated by the BAIID's sensing element, and calculates correction coefficients or other compensation based on the calibration test. This calibration data is stored in the BAIID, and in a further example is uploaded to the central computer so that an accuracy history of the BAIID can be reviewed to detect possible problems with the ethanol sensor and to document a history of reliable calibration of the device.

Once the calibration is complete and the calibration result data has been stored, the calibration station's controller installs operational firmware on the BAIID in place of the calibration firmware at 814, returning the BAIID to a state in which it can be installed in a vehicle and used to prevent people who are intoxicated from starting or driving a vehicle. The operational firmware in a more detailed example is validated, such as by ensuring that it has been correctly installed and the BAIID is functional when using the operational firmware, such as by booting the BAIID device. The operational firmware in a further example varies by jurisdiction, by user, or by other criteria, such as incorporating retesting and threshold data for a particular jurisdiction or permitting a reduced air volume for tests for a user who has reduced lung capacity. Removing calibration firmware and installing operational firmware before returning the BAIID to service also improves the security of the device, preventing a device that is not calibrated or that was removed during the calibration process from functioning as a BAIID should it be connected to the vehicle.

The calibration station in this example then performs various functional tests on the BAIID apart from calibration, such as verifying that the BAIID properly controls various attached vehicle systems such as a starter, fuel pump, or ignition, and accurately senses various information from the vehicle such as whether the vehicle is running. This is performed in this example through use of a car simulation module comprising a part of the calibration station, and these operational tests in an alternate example are performed while the BAIID has calibration firmware or other test-specific firmware installed.

After testing is complete, the calibration station indicates to the technician that the BAIID can be removed from the cradle and returned to service, and the technician reinstalls the BAIID in a vehicle. Should the BAIID fail testing or calibration, the technician is prompted to send the BAIID in for service, and an alternate BAIID is programmed with firmware and other information associating the BAIID with the particular user from whom the defective BAIID was received.

Returning to the example BAIID system of FIG. 3, vehicle electrical systems 302 are connected to BAIID system components 304. A Bluetooth relay 306 is also installed in the vehicle in place of a standard vehicle relay, as part of the BAIID system. The vehicle subsystem 302 comprises an OBDII diagnostic connector 308, which is connected to the vehicle's electronic control unit or ECU 310. In other examples, vehicle systems will provide an interface to a BAIID through cut and spliced wires, or through other methods.

The ECU in this example is connected to various electrical subsystems within the vehicle using a bus such as a car area network bus or CANBUS, including body control module (BCM) 312 and engine control module (ECM) 314. The BCM is coupled to electrical systems that are a part of the car's body and that are not integral to operation of the engine or powertrain, such as the radio 316, the horn 318, and the hazard lights 320. The ECM is coupled to electrical systems that are associated with the vehicle's engine or powertrain, such as the fuel pump 322, the ignition 324, and the starter 326. In other examples, other modules such as a powertrain control module (PCM) or the like will control various elements shown as controlled by the ECM or BCM in this example.

The vehicle-connected BAIID 304 includes a control module 328 and a detection unit 330, which are coupled to the vehicle through the vehicle's OBDII diagnostic connector 308. In this example, the control module 328 includes an OBDII interface to communicate with the vehicle, a processor 334 to execute program instructions, and storage 336 to store program code used to implement various BAIID functions. The control module also includes a wireless Bluetooth communications module 338, a Universal Serial Bus (USB) module 340, and an RS232 serial port 342. Although some examples include more, fewer, or different communication modules than those shown at 338-342, the communication modules illustrated here are representative of typical communication modules as may be used to implement various examples. In other examples, the control module 328 is connected to vehicle systems using other methods, such as by cutting and splicing wires leading to vehicle systems under control of the BAIID, such as the starter motor, fuel pump, and other such systems.

The detection unit 330 in this example includes a display 344 operable to display text or graphics to a user, and a fuel cell 346 or other detection element operable to detect the presence and/or level of an intoxicant. In a more detailed example, a fuel cell operable to detect the level of ethanol in a user's breath is employed. The detection unit 330 is coupled to the control module through connection 348, which in this example is a RS232 serial connection, but in alternate embodiments is a Bluetooth wireless connection or other suitable connection. The detection unit in this example comprises the handheld of FIG. 2, such that a user may pick the unit up to facilitate conducting a breath test using the fuel cell 346. In a further example, one or more elements of control module 328 are also integrated into the handheld of FIG. 2, such that the handheld includes functionality of both control module 328 and detection unit 330. Because calibration typically involves testing the fuel cell 346 as well as downloading operational data and programming calibration information using elements such as storage 336, elements including both detection unit and control module functionality will be returned to an authorized servicer for periodic calibration.

To install the BAIID 304 in the vehicle of FIG. 2, the control module 328 is coupled to the vehicle's electrical system by connecting the OBDII interface 332 of the control module to the OBDII diagnostic connector 308 of the vehicle (also shown as OBDII diagnostic connector 102 of FIG. 1). This is achieved by simply connecting a cable extending from the control module to the vehicle's OBDII port in some embodiments. Other embodiments will use a wireless connection such as a Bluetooth transceiver coupled to the vehicle's OBDII diagnostic connector in communication with the Bluetooth module 338 of the control module. This step of connecting the control module 328 to the OBDII connector 308 does not require the use of any tools and can be performed with the installer's hands by pushing the cable extending form the control module into the vehicle's OBDII port 308, or by pushing the Bluetooth transceiver into the vehicle's OBDII port 308. This facilitates easy removal and installation of the control module and detection unit for calibration, reducing the time and cost associated with periodic calibrations of the BAIID.

In a further example, the Bluetooth relay 306 is also installed in the vehicle, enabling the control module 328 to selectively allow operation of the Bluetooth relay 306. The Bluetooth relay 306 is installed by removing one of the standard vehicle relays and replacing it with the Bluetooth relay 306. In other examples, a wired replacement relay is used rather than Bluetooth relay 306, or wiring to vehicle elements such as fuel pump 322, ignition 324, and starter 326 is selectively interrupted through other means such as a relay box or cut and spliced wiring coupled to the control module.

In operation, the control module 328 uses a processor 334 and other circuitry to perform basic ignition interlock functions. The control module is connected to a detection unit 330 that is operable to perform functions such as display a current status or provide instructions to a user using display 344, and to receive a breath sample for analysis using fuel cell 346 or another such detection element. The detection unit and control module are shown as separate elements in the example of FIG. 3, but in other examples can be integrated into the same physical unit, can be implemented in whole or in part using other devices such as a user's smartphone, and may include fewer or additional features from the example shown here.

To start a vehicle, a user typically turns the vehicle key to the run position to power the vehicle systems, while the control module is powered continuously through the vehicle's OBDII diagnostic connector. When the control module detects activity on one or more of the vehicle's communication busses, it initiates communication with the vehicle and prompts for a start breath sample. The procedure in one example includes prompting a user via the display 344 to blow a breath into the BAIID that is sufficiently long and has a sufficient volume of air to verify that the user is not intoxicated, such as having an ethanol level in breath that is lower than a preset threshold. If the user's breath passes the intoxication test, the control module signals the vehicle to enable the vehicle to start, such as by enabling one or more vehicle systems that have been previously disabled via the OBDII diagnostic connector or signaling Bluetooth relay 306 to enable the relay to operate normally.

If the user's breath passes the test, the control module selectively enables operation of the vehicle. In an example where the user's breath does not pass the test, the control module does not allow the vehicle to start, and records a violation or a failed test. The control module prevents the vehicle from starting in one example by leaving the Bluetooth relay 306 in a deactivated mode or putting the Bluetooth relay 306 into a deactivated mode such that it does not function as a normal relay. In another example, the control module prevents the vehicle from starting by writing or leaving a portion of firmware of one of the vehicle's control systems modified such that the vehicle is inoperable. In another example, the control module prevents the vehicle from starting by disabling a vehicle system such as the fuel pump, ignition, starter, etc. via the OBDII diagnostic connector or through other mechanisms.

Once the vehicle is in operation, the control module will occasionally and randomly prompt the user for a retest sample. Such a retest requires the driver to provide another breath sample to the detection unit 330. Although official documentation suggests that the retest be conducted after the driver has pulled off the road and stopped the vehicle, the Federal Register recognizes that 99% of retests are done while the vehicle remains in normal operation. When the driver is prompted to provide a retest sample, the driver typically must deliver the retest sample within a relatively short time, such as a minute or several minutes, or the control module 328 may take various actions to encourage the driver to complete the retest or restrict operation of the motor vehicle.

In one such example, the control module 328 responds to a failed retest or a retest not completed in a timely manner by providing an indication that the retest has not been successfully completed, such as by honking the horn 318 or flashing the hazard lights 320. In a further example, the radio 316 is turned down to a minimal volume level or is turned off to make audible prompts to complete a retest more easily recognized. In another example, the controller responds to failure to complete a retest by restricting vehicle operation, such as by gradually reducing vehicle speed to a governed speed that enables the driver to safely control and stop the vehicle.

The ignition interlock system of FIG. 3 shows a system in which a control module 328 and a detection unit 330 that are either separate items or are combined into a single unit may be structured. Other examples will use other configurations, such as incorporation of additional or legacy functions from preexisting BAIID systems which are designed to be installed by the preexisting methods of cutting holes in the firewall, cutting and splicing wires, and routing wiring from the control module to various electrical systems within the vehicle. Such configurations may include wiring harnesses including plugs and sockets that are concealed from the user, but that facilitate easier removal and replacement of a BAIID for periodic calibration.

These examples show how an ignition interlock device calibration station can incorporate various features to ensure secure handling of data and accurate calibration using compressed dry gas in an installer's shop environment. The systems and methods presented here may be implemented in part using a computerized device, such as a smartphone, handheld, or other computerized device.

Figure 9:
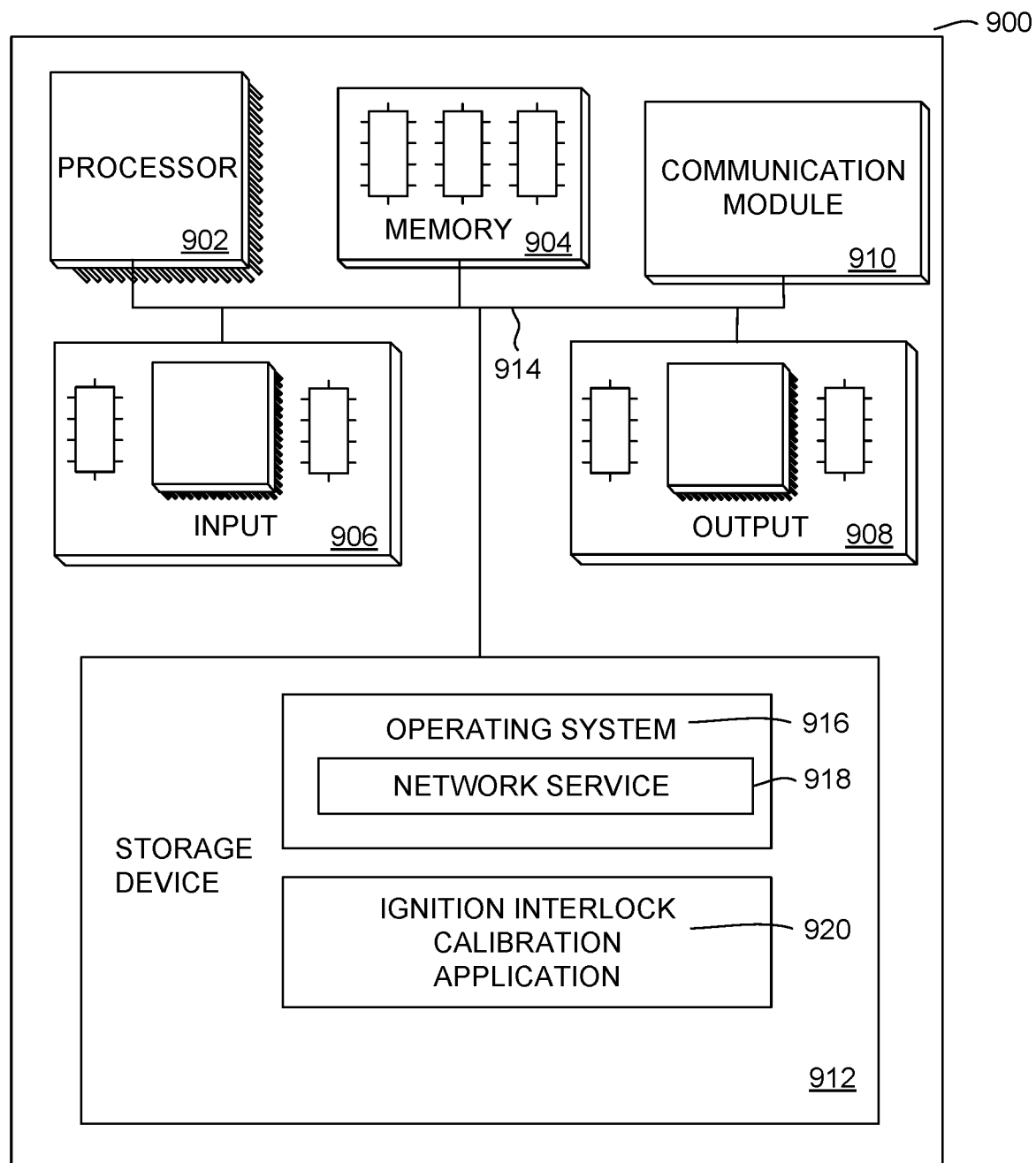
FIG. 9 shows a computerized calibration station or component of a calibration station, consistent with various examples described herein.

FIG. 9 shows a computerized calibration station or component of a calibration station, consistent with various examples described herein. FIG. 9 illustrates only one particular example of computing device 900, and other computing devices 900 may be used in other embodiments. Although computing device 900 is shown as a standalone computing device, computing device 900 may be any component or system that includes one or more processors or another suitable computing environment for executing software instructions in other examples, and need not include all of the elements shown here. A controller 400, control module, relay box and detection unit as described herein are examples of components that can be implemented using computing devices such as computing device 900.

As shown in the specific example of FIG. 9, computing device 900 includes one or more processors 902, memory 904, one or more input devices 906, one or more output devices 908, one or more communication modules 910, and one or more storage devices 912. Computing device 900, in one example, further includes an operating system 916 executable by computing device 900. The operating system includes in various examples services such as a network service 918. One or more applications, such as an ignition interlock application 820 are also stored on storage device 912, and are executable by computing device 900.

Each of components 902, 904, 906, 908, 910, and 912 may be interconnected (physically, communicatively, and/or operatively) for inter-component communications, such as via one or more communications channels 914. In some examples, communication channels 914 include a system bus, network connection, inter-processor communication network, or any other channel for communicating data. Applications such as ignition interlock calibration application 920 and operating system 916 may also communicate information with one another as well as with other components in computing device 900.

Processors 902, in one example, are configured to implement functionality and/or process instructions for execution within computing device 900. For example, processors 902 may be capable of processing instructions stored in storage device 912 or memory 904. Examples of processors 902 include any one or more of a microprocessor, a controller, a digital signal processor (DSP), an application specific integrated circuit (ASIC), a field-programmable gate array (FPGA), or similar discrete or integrated logic circuitry.

One or more storage devices 912 may be configured to store information within computing device 900 during operation. Storage device 912, in some examples, is known as a computer-readable storage medium. In some examples, storage device 912 comprises temporary memory, meaning that a primary purpose of storage device 912 is not long-term storage. Storage device 912 in some examples includes a volatile memory, meaning that storage device 912 does not maintain stored contents when computing device 900 is turned off. In other examples, data is loaded from storage device 912 into memory 904 during operation. Examples of volatile memories include random access memories (RAM), dynamic random access memories (DRAM), static random access memories (SRAM), and other forms of volatile memories known in the art. In some examples, storage device 912 is used to store program instructions for execution by processors 902. Storage device 912 and memory 904, in various examples, are used by software or applications running on computing device 900 such as ignition interlock application 920 to temporarily store information during program execution.

Storage device 912, in some examples, includes one or more computer-readable storage media that may be configured to store larger amounts of information than volatile memory. Storage device 912 may further be configured for long-term storage of information. In some examples, storage devices 912 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 900, in some examples, also includes one or more communication modules 910. Computing device 900 in one example uses communication module 910 to communicate with external devices via one or more networks, such as one or more wireless networks. Communication module 910 may be a network interface card, such as an Ethernet card, an optical transceiver, a radio frequency transceiver, or any other type of device that can send and/or receive information. Other examples of such network interfaces include Bluetooth, 3G or 4G, WiFi radios, and Near-Field Communications (NFC), and Universal Serial Bus (USB). In some examples, computing device 900 uses communication module 910 to wirelessly communicate with an external device such as via public network such as the Internet.

Computing device 900 also includes in one example one or more input devices 906. Input device 906, in some examples, is configured to receive input from a user through tactile, audio, or video input. Examples of input device 806 include a touchscreen display, a mouse, a keyboard, a voice responsive system, video camera, microphone or any other type of device for detecting input from a user.

One or more output devices 908 may also be included in computing device 900. Output device 908, in some examples, is configured to provide output to a user using tactile, audio, or video stimuli. Output device 908, in one example, includes a display, a sound card, a video graphics adapter card, or any other type of device for converting a signal into an appropriate form understandable to humans or machines. Additional examples of output device 908 include a speaker, a light-emitting diode (LED) display, a liquid crystal display (LCD), or any other type of device that can generate output to a user.

Computing device 900 may include operating system 916. Operating system 916, in some examples, controls the operation of components of computing device 900, and provides an interface from various applications such ignition interlock calibration application 920 to components of computing device 900. For example, operating system 916, in one example, facilitates the communication of various applications such as ignition interlock application 920 with processors 902, communication unit 910, storage device 912, input device 906, and output device 908. Applications such as ignition interlock calibration application 920 may include program instructions and/or data that are executable by computing device 900. As one example, ignition interlock calibration application 920 may include instructions that cause computing device 900 to perform one or more of the operations and actions described in the examples presented herein.

Although specific embodiments have been illustrated and described herein, any arrangement that achieve the same purpose, structure, or function may be substituted for the specific embodiments shown. This application is intended to cover any adaptations or variations of the example embodiments of the invention described herein. These and other embodiments are within the scope of the following claims and their equivalents.

The invention claimed is:

1. A breath alcohol device calibration system, comprising:
an internal alcohol sensor configured to measure an alcohol concentration of a gas in a reference gas tank;
a controller configured to:
receive a specified expected reference alcohol concentration of the gas in the reference gas tank by downloading the specified expected reference alcohol concentration from a central remote server,
measure the alcohol concentration of the gas in the reference gas tank using the internal alcohol sensor,
compare the measured alcohol concentration of the gas in the reference gas tank measured by the internal alcohol sensor with the specified expected reference alcohol concentration,
verify that the measured alcohol concentration of the gas in the reference gas tank measured by the internal alcohol sensor is at or within a threshold variation of the specified expected reference alcohol concentration,
indicate an error if the measured alcohol concentration of the gas in the reference gas tank measured by the internal alcohol sensor varies from the specified expected reference alcohol concentration by the threshold variation, and
calibrate an alcohol detection element of a candidate breath alcohol device by:
measuring an alcohol concentration of the gas in the reference gas tank with the alcohol detection element,
comparing the measured alcohol concentration of the gas in the reference gas tank measured by the alcohol detection element with the specified expected reference alcohol concentration, and
adjusting the candidate breath alcohol device such that measured alcohol concentration of gas in the reference gas tank measured by the alcohol detection element corresponds to the specified expected reference alcohol concentration;
a networking element that enables a network connection to the central remote server; and
an electronic data connection to the candidate breath alcohol device enabling retrieval of data from the candidate breath alcohol device.

2. The breath alcohol device calibration system of claim 1, wherein the threshold variation is one of 0.5%, 1%, 2%, 3%, or 5% variation.

3. The breath alcohol device calibration system of claim 1, wherein the internal alcohol sensor comprises a fuel cell.

4. The breath alcohol device calibration system of claim 1, further comprising a base and a tank cradle coupled to the base, wherein the internal alcohol sensor is disposed within the base.

5. The breath alcohol device calibration system of claim 4, wherein the internal alcohol sensor is connected to the tank cradle via a hose.

6. The breath alcohol device calibration system of claim 1, wherein the controller is configured to allow drift of the internal alcohol sensor.

7. The breath alcohol device calibration system of claim 1, further comprising a pressure gauge and an electronic pressure transducer which are configured to indicate a pressure inside the reference gas tank.

8. The breath alcohol device calibration system of claim 1, further comprising a cradle for the candidate breath alcohol device.

9. The breath alcohol device calibration system of claim 8, wherein the internal alcohol sensor is in fluid communication with the cradle for the candidate breath alcohol device.

10. The breath alcohol device calibration system of claim 1, wherein the specified expected reference alcohol concentration is labeled on the reference gas tank.

11. The breath alcohol device calibration system of claim 1, further comprising a hose that connects the reference gas tank to the internal alcohol sensor, wherein the hose is configured such that reference gas flowing through the internal alcohol sensor is provided to the alcohol detection element of the candidate breath alcohol device.

12. The breath alcohol device calibration system of claim 1, wherein the controller is programmed with the specified expected reference alcohol concentration prior to measuring the alcohol concentration of the reference gas.

13. The breath alcohol device calibration system of claim 1, wherein the candidate breath alcohol device is programmed with the specified expected reference alcohol concentration prior to measuring the alcohol concentration of the reference gas.

14. The breath alcohol device calibration system of claim 1, wherein the specified expected reference alcohol concentration for the gas in the reference gas tank is downloaded from the central remote server using a WiFi connection.

15. The breath alcohol device calibration system of claim 1, wherein a reference gas antenna is operable to read at least one of an RFID (Radio Frequency Identification) or an NFC (Near Field Communication) label attached to the reference gas tank that is coupled to the breath alcohol device calibration system.

16. The breath alcohol device calibration system of claim 1, wherein the controller is further operable to read a temperature history of the reference gas tank from an electronic device coupled to the reference gas tank.

17. The breath alcohol device calibration system of claim 16, wherein the electronic device is thermally coupled to a body of the reference gas tank and is operable to measure and record temperature of the reference gas tank over time.

18. The breath alcohol device calibration system of claim 16, wherein the controller is further operable to measure a pressure of the gas in the reference gas tank, and to use the temperature history of the reference gas tank read from the electronic device and the measured pressure compared to an expected pressure for the reference gas tank to determine whether the reference gas tank may have been opened while the temperature of the tank was impermissibly low.

19. A breath alcohol device calibration system, comprising:
   a first reference gas tank containing a first reference gas, the first reference gas having a first alcohol concentration;
   a second reference gas tank containing a second reference gas, the second reference gas having a second alcohol concentration that is different from the first alcohol concentration;
   a receptacle of the calibration system configured to interchangeably attach to one of the first reference gas tank and the second reference gas tank and to form a gas connection to an attached reference gas tank;
   an internal alcohol sensor of the calibration system configured to measure an alcohol concentration of the attached reference gas tank; and
   a controller of the calibration system configured to:
      receive a specified expected reference alcohol concentration of an attached reference gas tank, selected from the first reference gas tank and the second reference gas tank, by downloading the specified expected reference alcohol concentration from a central remote server,
      measure the alcohol concentration of the first reference gas or the second reference gas in the attached reference gas tank using the internal alcohol sensor,
      compare the measured alcohol concentration of the first reference gas or the second reference gas with the specified expected reference alcohol concentration,
      verify that the measured alcohol concentration of first reference gas or the second reference gas measured by the internal alcohol sensor is at or within a threshold variation of the specified expected reference alcohol concentration,
      indicate an error if the measured alcohol concentration of the first reference gas or the second reference gas measured by the internal alcohol sensor varies from the specified expected reference alcohol concentration by the threshold variation, and
      calibrate an alcohol detection element of a candidate breath alcohol device using the first reference gas or the second reference gas of the attached reference gas tank.

20. The breath alcohol device calibration system of claim 19, further comprising:
   a networking element that enables a network connection to the central remote server; and
   an electronic data connection to the candidate breath alcohol device enabling retrieval of data from the candidate breath alcohol device;
   wherein calibrating an alcohol detection element of the candidate breath alcohol device using the first reference gas or the second reference gas of the attached reference gas tank further comprises:
   measuring an alcohol concentration of the first reference gas or the second reference gas in the attached reference gas tank with the alcohol detection element,
   comparing the measured alcohol concentration of the first reference gas or the second reference gas in the attached reference gas tank measured by the alcohol detection element with the specified expected reference alcohol concentration, and
   adjusting the candidate breath alcohol device such that measured alcohol concentration of gas in the attached reference gas tank measured by the alcohol detection element corresponds to the specified expected reference alcohol concentration.

\* \* \* \* \*